US011627879B2

(12) United States Patent
Mak et al.

(10) Patent No.: US 11,627,879 B2
(45) Date of Patent: *Apr. 18, 2023

(54) MULTI-FUNCTIONAL HANDHELD OPTICAL COHERENCE TOMOGRAPHY IMAGING SYSTEM

(71) Applicant: SYNAPTIVE MEDICAL INC., Toronto (CA)

(72) Inventors: Siu Wai Jacky Mak, Toronto (CA); Ho Yiu Kyle Cheng, Toronto (CA); Fangxin Li, Toronto (CA); Harshul Varma, Toronto (CA)

(73) Assignee: Synaptive Medical Inc.

( * ) Notice: Subject to any disclaimer, the term of this patent is extended or adjusted under 35 U.S.C. 154(b) by 166 days.

This patent is subject to a terminal disclaimer.

(21) Appl. No.: 17/236,634

(22) Filed: Apr. 21, 2021

(65) Prior Publication Data

US 2021/0275027 A1  Sep. 9, 2021

Related U.S. Application Data

(63) Continuation of application No. 15/637,045, filed on Jun. 29, 2017, now Pat. No. 11,026,580.

(51) Int. Cl.
*A61B 5/00* (2006.01)
*A61B 46/10* (2016.01)
(Continued)

(52) U.S. Cl.
CPC .......... *A61B 5/0066* (2013.01); *A61B 5/0042* (2013.01); *A61B 34/10* (2016.02);
(Continued)

(58) Field of Classification Search
CPC ........ A61B 17/3421; A61B 2034/2051; A61B 2034/2055; A61B 2090/103; A61B 2090/3735; A61B 2560/0425; A61B 2560/0431; A61B 2560/0443; A61B 2562/0233; A61B 2576/026; A61B 34/10;
(Continued)

(56) References Cited

U.S. PATENT DOCUMENTS

2013/0345558 A1* 12/2013 Boppart ............. G01B 9/02054
600/425

OTHER PUBLICATIONS

Mak, Siu Wai Jacky, et al., "Multi-Functional Handheld Optical Coherence Tomography Imaging System", U.S. Appl. No. 15/637,045, filed Jun. 29, 2017.

* cited by examiner

*Primary Examiner* — Michael T Rozanski

(57) ABSTRACT

An OCT (Optical Coherence Tomography) handheld device is provided comprising: a housing configured for handheld OCT scanning during a surgical procedure, the housing comprising an OCT scanning end and a proximal end opposite the OCT scanning end; an OCT scanning device inside the housing, the OCT scanning device configured for one or more of OCT polarized scanning and Doppler OCT scanning from the OCT scanning end, the OCT scanning device further configured to receive and convey OCT light between the proximal end and an OCT analysing system; and a tip extending from the OCT scanning end, the tip being removably attached to the OCT scanning end, the tip configured to receive and collect the OCT light therethrough. The OCT handheld device is configured to be removably draped around the tip, for use in the surgical procedure.

20 Claims, 18 Drawing Sheets

(51) Int. Cl.
  *A61B 34/20* (2016.01)
  *A61B 46/00* (2016.01)
  *A61B 90/10* (2016.01)
  *A61B 34/10* (2016.01)
  *A61B 90/00* (2016.01)
  A61B 17/34 (2006.01)
  A61B 34/30 (2016.01)

(52) U.S. Cl.
  CPC .............. *A61B 34/20* (2016.02); *A61B 46/10* (2016.02); *A61B 46/40* (2016.02); *A61B 90/10* (2016.02); *A61B 90/361* (2016.02); *A61B 90/37* (2016.02); *A61B 17/3421* (2013.01); *A61B 34/30* (2016.02); *A61B 2034/2051* (2016.02); *A61B 2034/2055* (2016.02); *A61B 2090/103* (2016.02); *A61B 2090/3735* (2016.02); *A61B 2560/0425* (2013.01); *A61B 2560/0431* (2013.01); *A61B 2560/0443* (2013.01); *A61B 2562/0233* (2013.01); *A61B 2576/026* (2013.01)

(58) Field of Classification Search
  CPC ......... A61B 34/20; A61B 34/30; A61B 46/10; A61B 46/40; A61B 5/0042; A61B 5/0066; A61B 90/10; A61B 90/361; A61B 90/37
  See application file for complete search history.

P-State En-Face Doppler OCT Image

1501

MULTI-FUNCTIONAL HANDHELD OPTICAL COHERENCE TOMOGRAPHY IMAGING SYSTEM

CROSS-REFERENCE TO RELATED APPLICATIONS

The present specification claims priority from U.S. patent Ser. No. 15/637,045, filed on Jun. 29, 2017, the entire contents of which is incorporated herein by reference.

FIELD

The specification relates generally to optical coherence tomography and specifically to a multi-functional handheld optical coherence tomography imaging system.

BACKGROUND

Optical Coherence Tomography (OCT) enables imaging of tissue to depths of typically 1-2 mm due to the light absorption and scattering property of tissue. However, the majority of OCT systems are table top systems which require tissue to be removed from a patient for OCT scanning. The process of removing tissue can cause severe damage to the patient, particularly when OCT scanning is to occur on human brain tissue. Furthermore, some OCT systems are purpose built for scanning particular body parts, such as OCT systems built for scanning human eyes only, in which a patients' head must be placed on purpose-built head holder for scanning. Indeed, such requirements are generally due to the stability needed to perform OCT scanning (e.g. the scanning tip and/or the tissue being scanned should be stable and/or lateral displacement during scanning should be minimal). Such stability can be especially important when performing Doppler OCT scanning and the like.

Such stability requirements can limit the usefulness of handheld OCT systems, which are generally limited to intensity based OCT scans that provide only a single mode structural contrast of the tissue based on its optical scattering. These handheld OCT systems provide no information about the level of tissue organization and can have very weak contrast on blood vessels. Neither do they give any quantitative information on blood flow. Furthermore, tips of handheld OCT systems are also too large to be inserted into a surgical opening and/or surgical access port for scanning in a neuro-surgical procedure. In particular, such handheld OCT systems are not stable enough to perform Doppler OCT scanning. For this reason, there is no OCT scanning probe for using surgical access ports in neuro-surgical procedures. In fact, there are no such handheld OCT systems suitable for many surgical environments, as such environments require that that medical devices used in surgery be sterile, which is difficult to do with handheld medical devices in general.

Some multi-contrast OCT systems can perform PS-OCT (polarization sensitive OCT) scanning to determine tissue organization. However, these systems either do not have the capability of imaging blood flow (e.g. using Doppler OCT scanning) and/or the capability of imaging a tissue's optical attenuation. While some of these systems also have PS-OCT imaging capability, stability issues again lead to poor scanning results, for example, due to polarization fluctuations that occur with non-polarization-maintaining fibers, for example, fiber movement, fiber stress and slight temperature changes. Hence, neither are such systems that are suitable for use in a clinical environment, suitable for use in an operating room. Furthermore, the tips and/or probes on these systems are also too large to be inserted into the surgical opening and/or surgical access ports used in neuro-surgical procedures.

SUMMARY

The present disclosure is generally directed to a handheld OCT device configured for one or more of OCT polarized scanning and Doppler OCT scanning, that is further configured for surgical draping, for example from a removable tip. The tip is further made from material that is both sterilisable and biocompatible, and can include a window, lens system, and the like. A surgical drape can be attached around an outer circumference of the tip, the surgical drape being sterilisable and configured to extend from the tip, over the handheld OCT device, and further over cables up to an OCT analyzing system. Hence, by attaching such a tip with a surgical drape to the OCT handheld device, the OCT handheld device can be rendered suitable for use in surgical environments. Furthermore, as the tip is sterilisable and biocompatible, and can include a window, lens system, and the like, the tip can be pressed against tissue in a surgical environment to provide the desired stability for performing one or more of OCT polarized scanning and Doppler OCT scanning. The tip can also be adapted for use with surgical access ports by configuring the dimensions of the tip to be compatible with surgical access ports (e.g. insertable through surgical access ports).

Hence, the present disclosure is generally directed to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

An aspect of the specification provides an OCT (Optical Coherence Tomography) handheld device comprising: a housing configured for handheld OCT scanning during a surgical procedure, the housing comprising an OCT scanning end and a proximal end opposite the OCT scanning end; an OCT scanning device inside the housing, the OCT scanning device configured for one or more of OCT polarized scanning and Doppler OCT scanning from the OCT scanning end, the OCT scanning device further configured to receive and convey OCT light between the proximal end and an OCT analysing system; and a tip extending from the OCT scanning end, the tip being removably attached to the OCT scanning end, the tip configured to receive and collect the OCT light therethrough, wherein the OCT handheld device is configured to be removably draped around the tip, for use in the surgical procedure.

In some implementations, the OCT handheld device further comprises a surgical drape attached around an outer circumference of the tip, the surgical drape configured to extend from the tip, over the housing and past the proximal end of the housing. In some implementations, the surgical drape is further configured to extend from the tip over the housing, past the proximal end, and over one or more cables extending from the proximal end to the OCT analysing system.

In some implementations, the tip further comprises one or more of a lens and a lens system.

In some implementations, the tip is removably attached to the OCT scanning end using one or more of: a bayonet mount; and a twist and lock attachment mechanism.

In some implementations, the tip is formed from one or more materials that are both sterilisable and biocompatible.

In some implementations, the tip is between about 0.5 inches and about 3 inches in length, and the tip has an outer diameter that is between about 1 mm and about 15 mm.

In some implementations, the tip is between about 3 inches and about 15 inches in length, and the tip has an outer diameter that is between about 1 mm and about 10 mm.

In some implementations, the OCT scanning end is configured for removeable attachment to one of a plurality of tips, each of the plurality of tips comprising a respective surgical drape attached around a respective outer circumference, the respective surgical drape configured to extend from a respective tip, over the housing and past the proximal end of the housing.

In some implementations, the OCT scanning device is further configured for polarized OCT scanning.

In some implementations, the OCT scanning device comprises one or more of: an OCT light scanning device, an OCT light delivery apparatus, and a light polarizing apparatus.

In some implementations, the OCT scanning device comprises polarization optics configured to polarize the OCT light. In some implementations, the polarization optics comprises a quarter waveplate. In some implementations, the OCT handheld device further comprises one or more polarization-maintaining optical fibers configured to convey the OCT light to and from the OCT analysing system.

In some implementations, the housing is configured to be held by a human hand.

The OCT handheld device of claim 1, wherein housing comprises one or more of a grip portion and slots, each configured for assisting a human hand with holding the housing.

In some implementations, the housing is angled between the OCT scanning end and the proximal end.

In some implementations, the OCT handheld device further comprises a tracking device.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Figure 1:
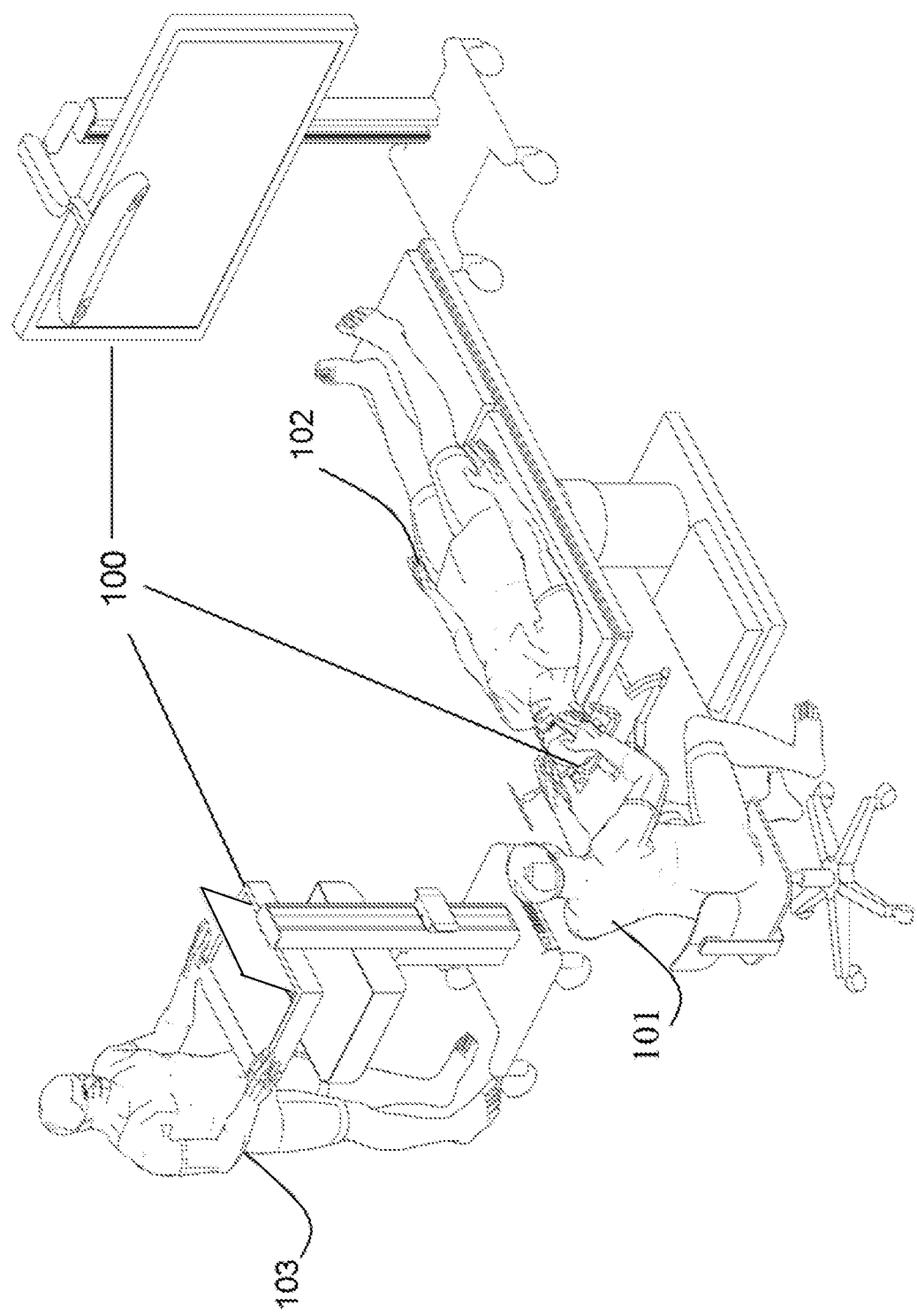
FIG. 1 shows an example operating room setup for a minimally invasive access port-based medical procedure, according to non-limiting implementations.

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . ." and "one or more . . ." language.

The terms "about", "substantially", "essentially", "approximately", and the like, are defined as being "close to", for example as understood by persons of skill in the art. In some implementations, the terms are understood to be "within 10%," in other implementations, "within 5%", in yet further implementations, "within 1%", and in yet further implementations "within 0.5%".

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
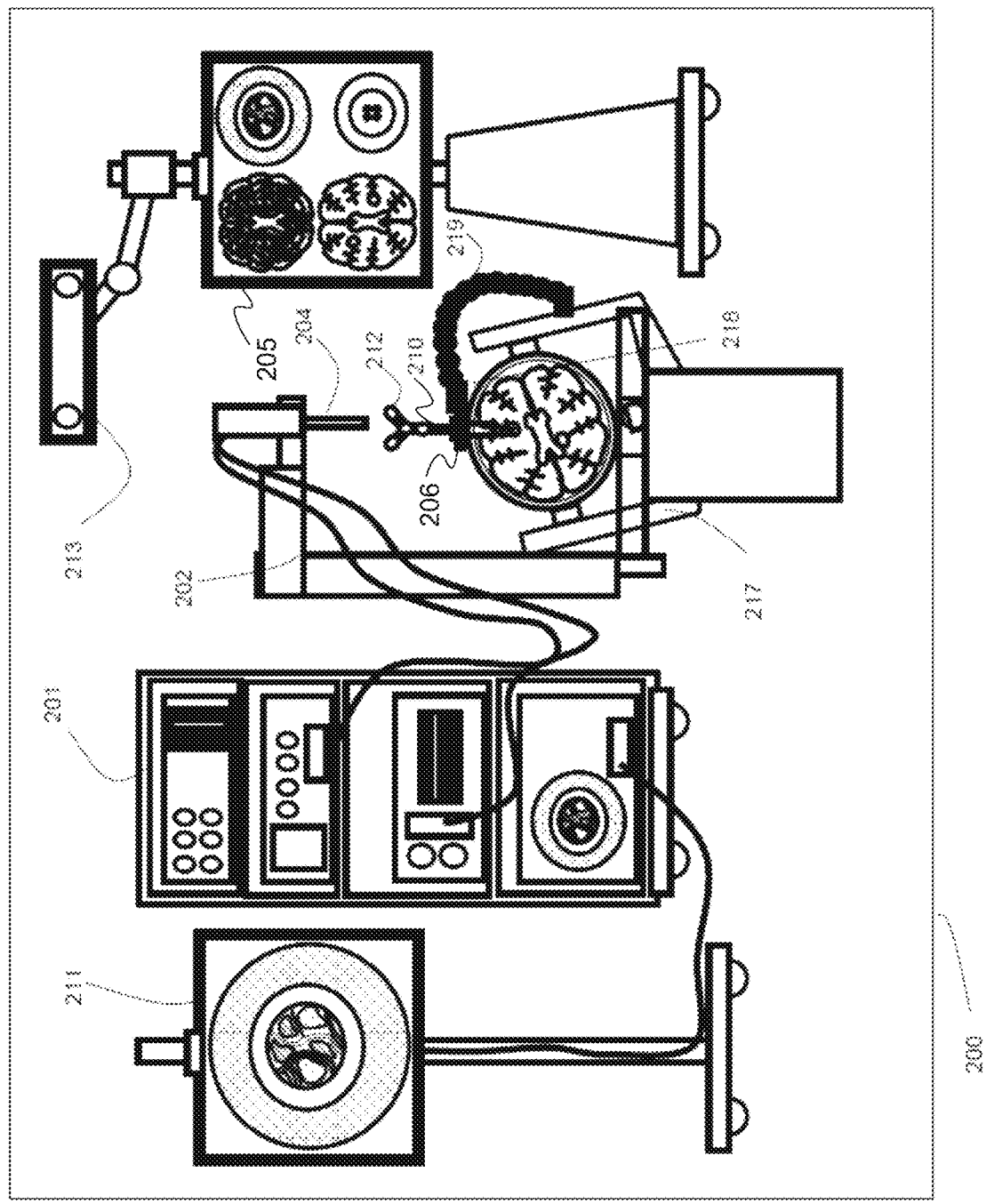
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
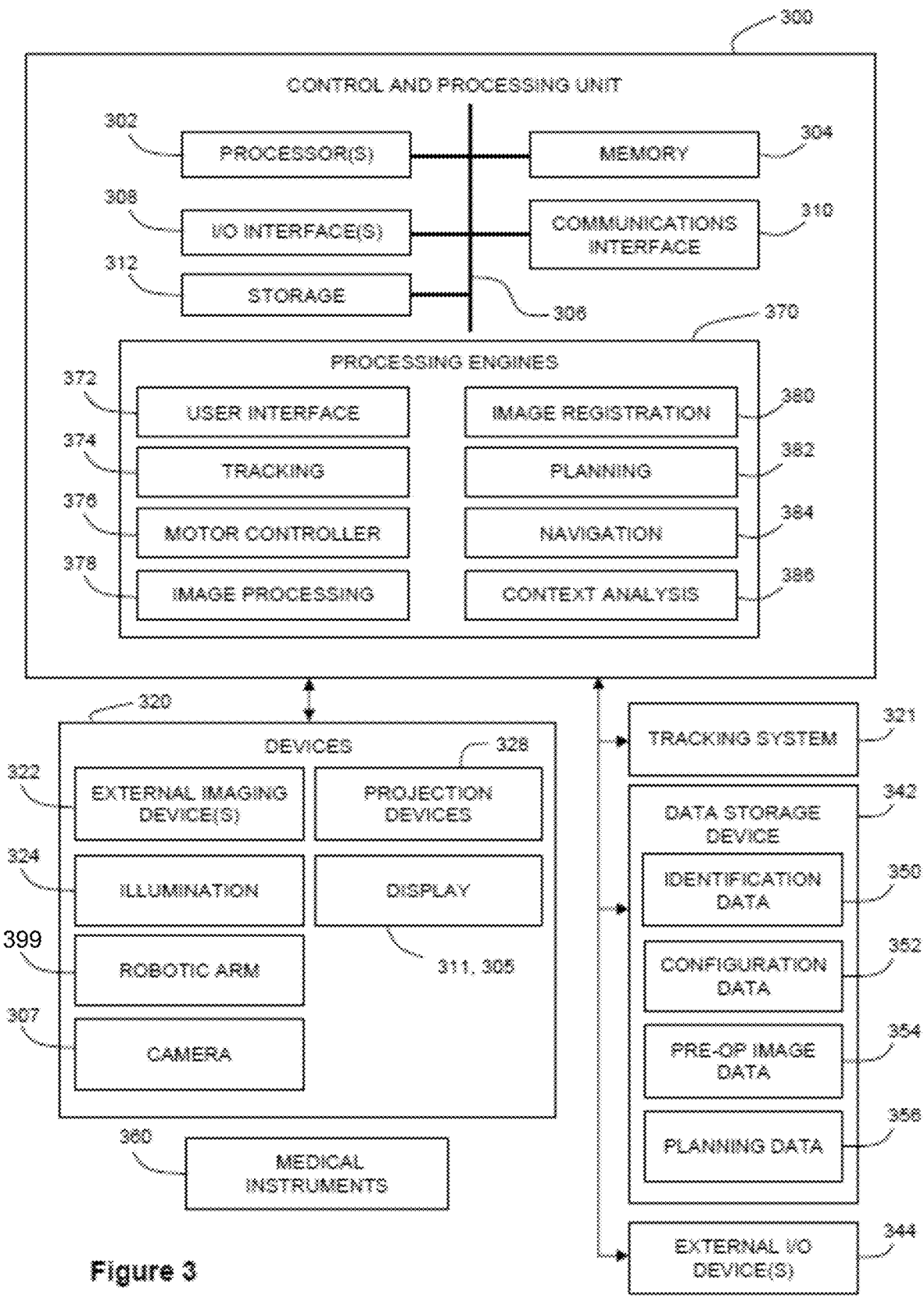
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm 399, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as read only memory (ROM), volatile random access memory (RAM), non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc.

While several examples have been provided, aspects of the present specification may be applied to other suitable medical procedures.

Figure 4:
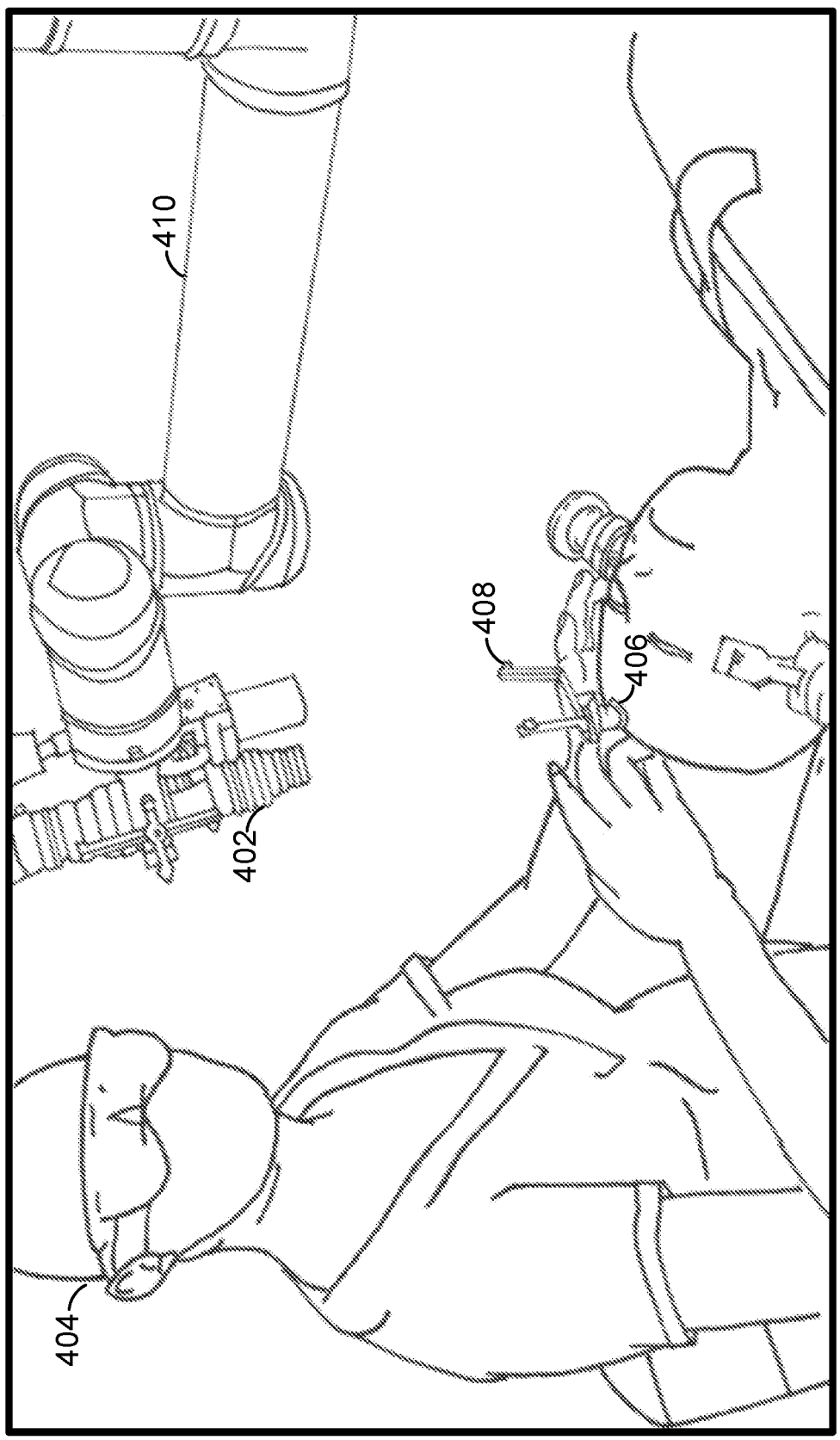
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
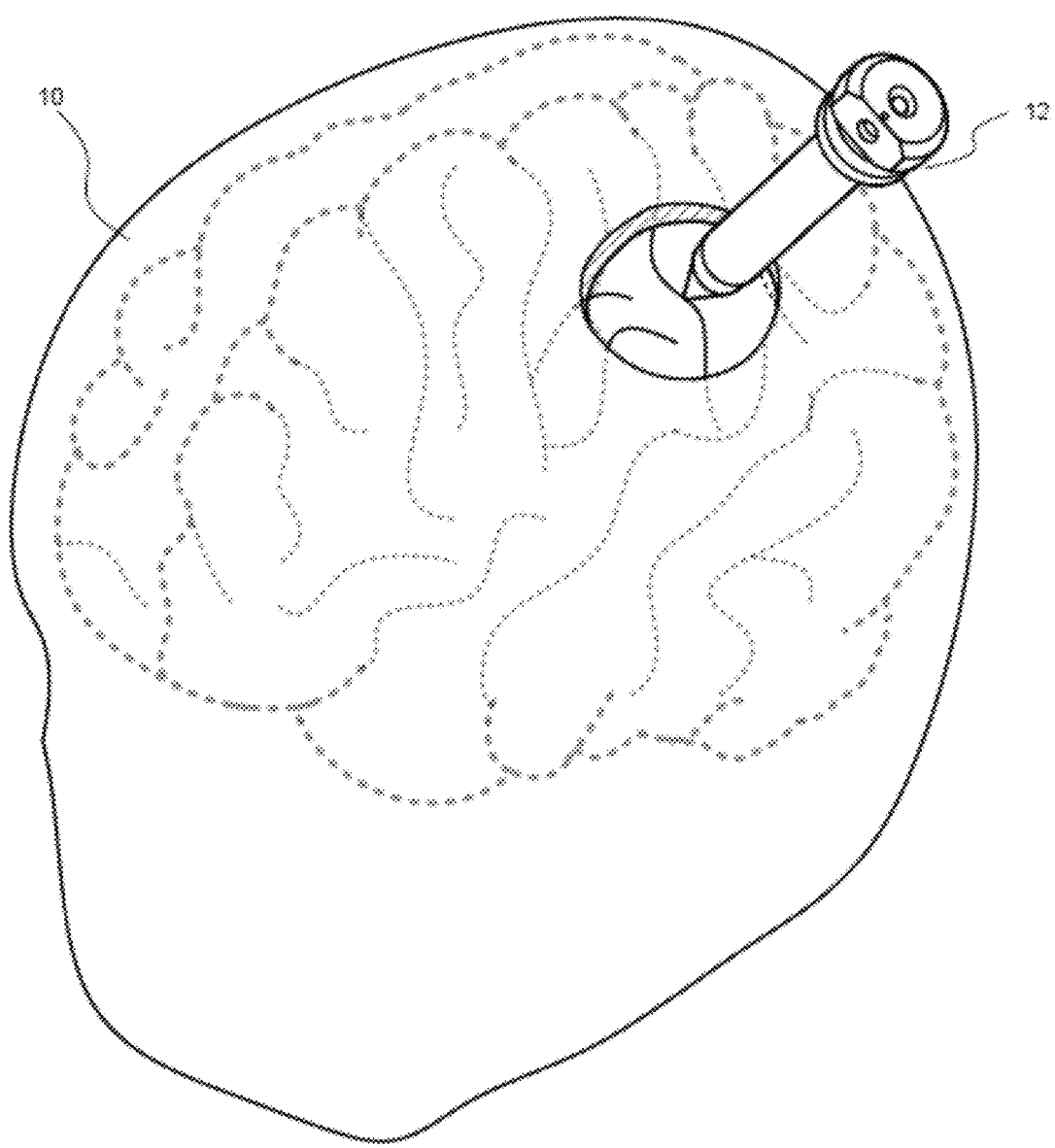
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
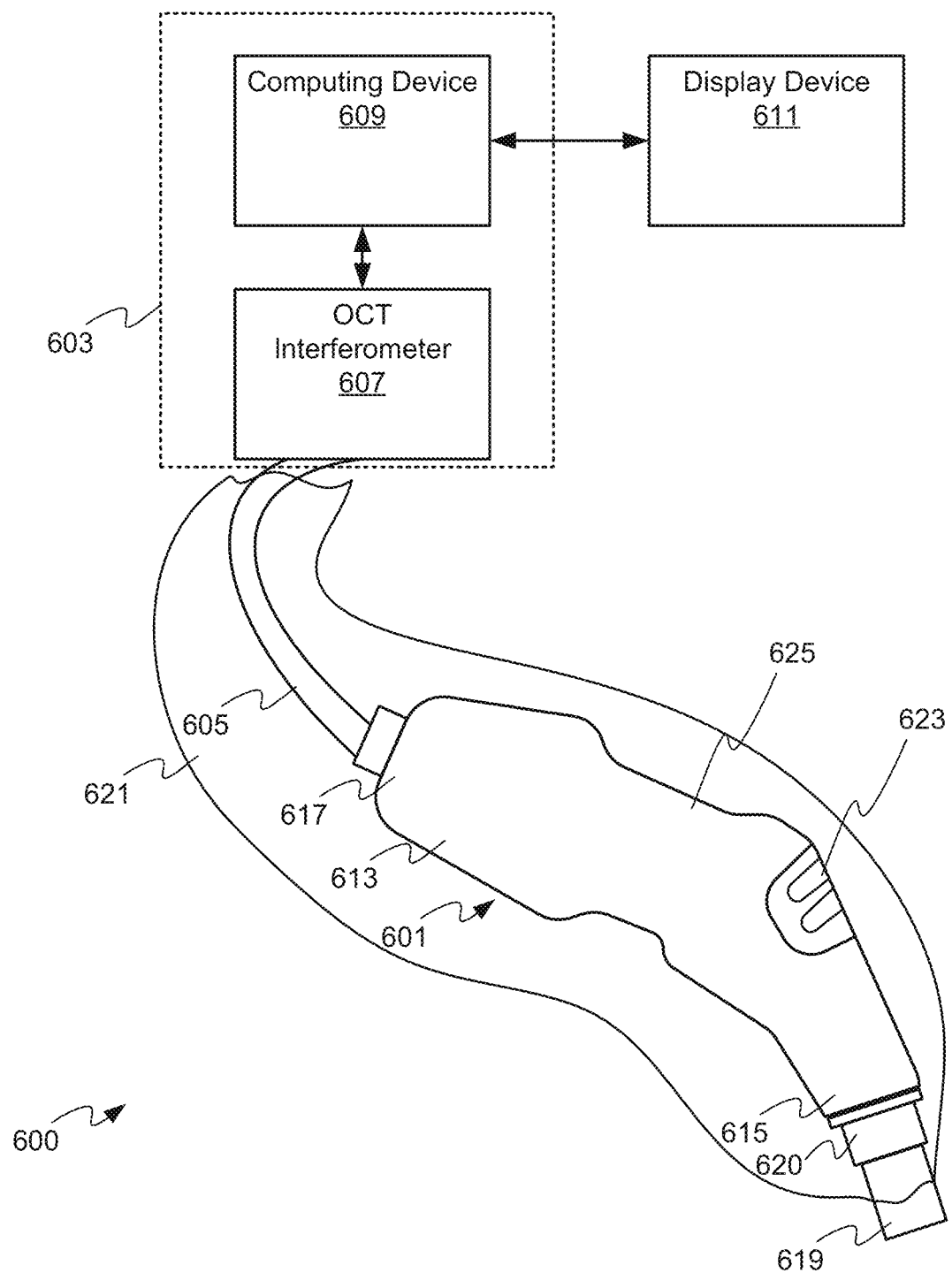
FIG. 6 depicts an OCT (Optical Coherence Tomography) system that includes a handheld OCT device, according to non-limiting implementations.

Attention is next directed to FIG. 6, which depicts an example of a surgical OCT system that includes a handheld OCT device that could be used with the access port 12 and/or in open case surgery.

Specifically, FIG. 6 depicts an optical coherence tomography (OCT) system 600 comprising: a handheld OCT device 601 (interchangeably referred to hereafter as the device 601) in communication with an OCT analyzing system 603 via one or more cables 605. The OCT analyzing system 603 comprises an OCT interferometer 607 and at least one computing device 609 configured to perform OCT analysis on OCT data received from the device 601. The system 600 further comprises at least one display device 611 in communication with the computing device 609, at least one display device 611 configured to visually display OCT images produced by the computing device 609, as described in further detail below. The display device 611 can be part of the OCT analyzing system 603, or a separate component, for example a component of a surgical system, including, but not limited to OCT system 600. Indeed, the OCT analyzing system 603 can also be a component of the OCT system 600. As such, the computing device 609 can be a component, for example, of the control and processing unit 300.

The device 601 comprises a housing 613 configured for handheld OCT scanning during a surgical procedure, the housing 613 comprising an OCT scanning end 615 and a proximal end 617 opposite the OCT scanning end 615. The proximal end 617 may be alternatively referred to as an OCT system end as it is the end of the housing 613 that is in communication with the OCT analysing system 603 As will be described below with respect to FIG. 8, the device 601 further comprises an OCT scanning device inside the housing, the OCT scanning device configured for one or more of OCT polarized scanning and Doppler OCT scanning from the OCT scanning end 615, the OCT scanning device further configured to receive and convey OCT light between the proximal end 617 and the OCT analysing system 603 (e.g. to and from the OCT interferometer 607). The device 601 further comprises a tip 619 extending from the OCT scanning end 615, the tip 619 being removably attached to the OCT scanning end 615, for example using an adaptor 620 at the OCT scanning end 615, the tip 619 configured to receive and collect OCT light therethrough.

The device 601 is generally configured to be removably draped around the tip 619, for use in a surgical procedure. For example, as depicted, the device 601 further comprises a surgical drape 621 attached around an outer circumference of the tip 619, the surgical drape 621, as depicted, configured to extend from the tip 619, over the housing 613 and past the proximal end 617 of the housing 613. In particular, as depicted, the surgical drape 621 is further configured to extend from the tip 619 over the housing 613, past the proximal end 617, and over the one or more cables 605 extending from the proximal end 617 to the OCT analysing system 603. Hence, when the device 601 is used with the surgical drape 621, and the tip 619 and the surgical drape 621 are both sterilized, the device 601 is quickly adaptable for use in a sterile surgical environment without, for example, having to sterilize the housing 613, the one or more cables 605 etc. However, the device 601 can also be used with tips that do not include a surgical drape.

The device 601, as depicted, further comprises one or more buttons 623, and the like which, when actuated can initiate an OCT scan by the device 601 and/or a mode of OCT scanning, for example one or more of OCT polarized scanning and Doppler OCT scanning, and/or OCT scanning without polarization or Doppler. In yet further implementations, actuation of one or more buttons 623 can initiate a background removal mode, for example to determine background noise which is removed in later OCT scans.

Figure 7:
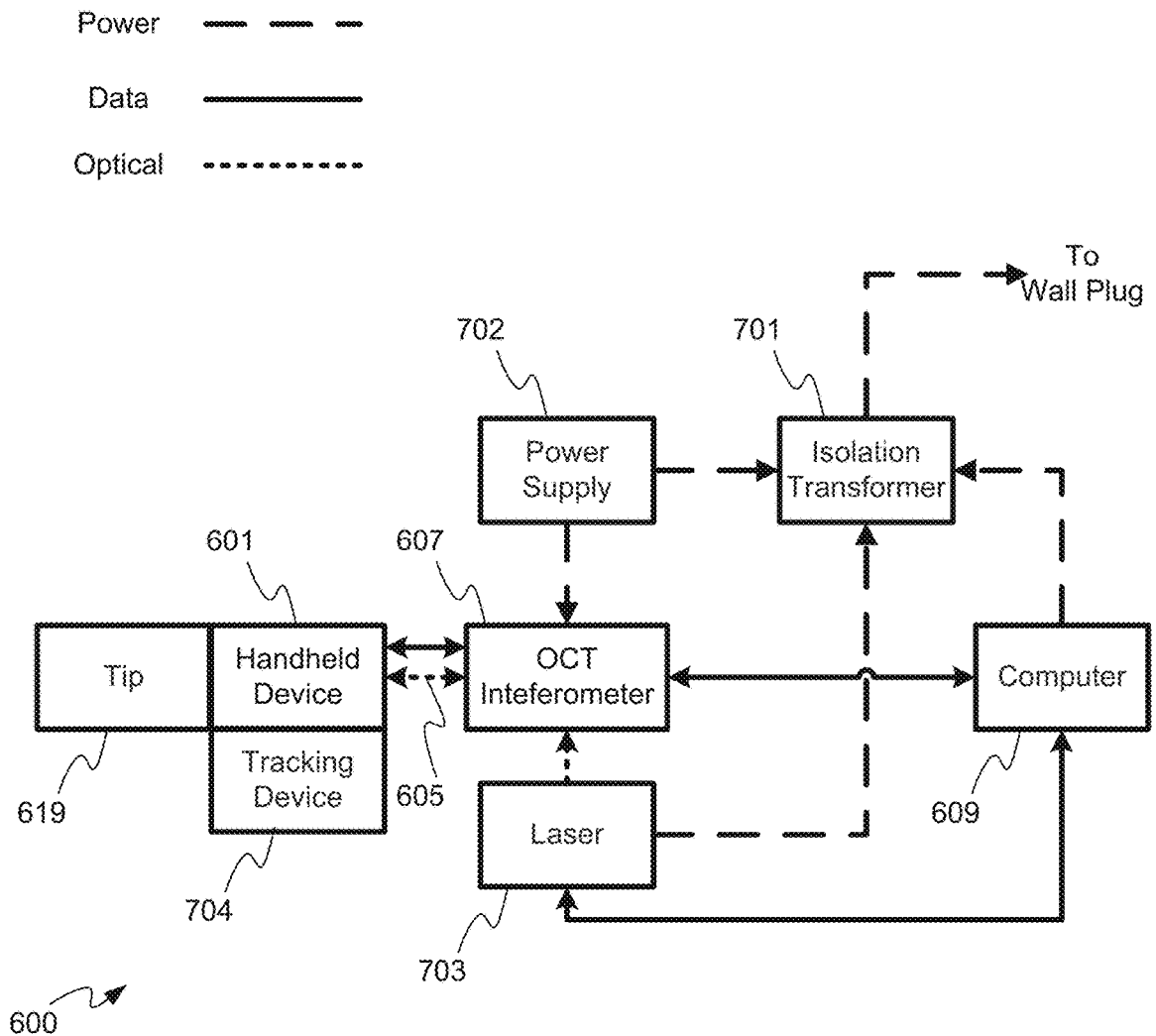
FIG. 7 depicts a block diagram of components of the OCT system of FIG. 6, according to non-limiting implementations.

Attention is next directed to FIG. 7 which depicts a schematic block diagram of the system 600 with electrical, optical and data connections between the components depicted as different line types (e.g. data connections are depicted as solid lines, power connections are depicted as coarsely broken lines, and optical connections are depicted as finely broken lines). As depicted, the system 600 further includes an isolation transformer 701 that receives power from a main power supply, for example via a wall plug, and the like, which supplies power to the computer 609, a power supply 702 for the OCT interferometer 607 and a laser 703 (which can be a component of the OCT interferometer 607 or separate component). Furthermore, as depicted, the tip 619 is mechanically attached to the device 601. As depicted an optional tracking device 704 is also mechanically attached to the device 601 described in further detail below with respect to FIG. 17.

The OCT interferometer 607 is configured to provided OCT light to the device 601 via the one or more cables 605, the one or more cables 605 including at least one optical fiber configured to convey OCT light between the device 601 and the OCT interferometer 607 (e.g. the optical connection between the device 601 and the OCT interferometer 607 depicted in FIG. 7). The OCT interferometer 607 may comprise a light source, such as the laser 703, or, as depicted, is in optical communication with the laser 703 external to the OCT interferometer 607, via one or more optical couplers and/or beam splitters etc. The OCT interferometer 607 includes a reference arm which may comprise at least a reference mirror, and a detector. The laser 703 may be directed to an optical coupler and/or beam splitter which splits the OCT light (e.g. laser light) into the reference arm and a sample arm of the OCT interferometer 607. In the reference arm of the OCT interferometer 607, the OCT light is directed to a mirror that sets a reference imaging distance from an optical coupler and/or beam splitter. The OCT light then reflects back to the optical coupler and/or beam splitter. In the sample arm, the optical coupler and/or beam splitter directs the OCT light to the device 601 for use in an OCT scan through the tip 619.

In some implementations, described below, the device 601 includes components which polarize the OCT light and performs polarized OCT scanning (which can also be referred to as polarization-sensitive OCT (PS-OCT) scanning). As such, in these implementations, the at least one optical fiber of the one or more cables 605 includes at least one polarization-maintaining (PM) optical fiber to convey polarized OCT light to and from the OCT interferometer 607. Furthermore, in these implementations, the OCT interferometer 607 includes components that analyse the polarization states (e.g. the s-state and the p-state) of the OCT light received from the device 601. For example, the reference arm and the sample arm of the OCT interferometer can be adapted to interfere the s-state OCT polarized light and the p-state OCT polarized light with reference s-state polarized light and reference p-state polarized light, respectively.

Furthermore, the OCT scanning and/or a mode thereof, can be initiated upon actuation of the one or more buttons 623. As a mode of OCT scanning can, in some instances, depend on setting at the OCT interferometer 607 and/or the computing device 609, the one or more cables 605 can include an electrical cable configured to relay data and/or signals indicative of a mode of OCT scanning to the OCT interferometer 607 and/or the computing device 609.

In any event, OCT light that is emitted from the tip 619, and reflected back through the tip 619, for example from tissue being scanned, is relayed back through the device 601 to the OCT interferometer 607. The reflected OCT light from device 601 and the reference mirror then interferes (e.g. for each polarization state, when the reflected OCT light is polarized) and forms a fringe pattern which creates an A-scan OCT signal through Fourier transform. The fringe pattern is converted to data using an imaging device, and the data is received at the computing device 609, which can convert the data into an image that is renderable at the display device 611 (assumed to be in communication with computing device 609 in FIG. 7, though not depicted). One such method for converting the data to an image is described below with respect to FIG. 18.

In some implementations, where the OCT light is not polarized by the device 601, the computing device 609 can produce OCT images with or without Doppler OCT analysis; in the case of Doppler OCT analysis, OCT scans from adjacent pixels are compared by the computing device 609 to produce a Doppler OCT image. In some implementations where the OCT light is polarized by the device 601, the computing device 609 can produce polarized OCT images for each of two polarization states (e.g. without Doppler OCT analysis). In some implementations where the OCT light is polarized by the device 601, the computing device 609 can produce Doppler OCT images for each of the two polarization states. For example, the two polarization states can comprise a "p" polarization state and an orthogonal "s" polarization state. Different information can be extracted from Doppler OCT images, and polarization sensitive OCT retardance images (with or without Doppler).

Attention is next directed briefly back to FIG. 6 for further discussion of the device 601. In particular, the opposing ends 615, 617 respectively comprise a distal end and a proximal end, with the proximal end 617 being an end that will be proximal a surgeon and the like, when system 600 is in use, and the distal end 615 being an end that will be distal the surgeon, and/or directed towards tissue, a sample, a patient being operated on, and the like, when system 600 is in use. For example, the distal end 615 of the device 601 is an end distal a surgeon using the device 601.

In some implementations, the device 601 and the tip 619 may be configured to perform OCT scanning through a surgical access port. However, in other implementations, the device 601 and the tip 619 may be configured for use with one or more of an image guided medical procedure, and a minimally invasive procedure.

The device 601 may comprise one or more of an external handheld OCT device, an exoscope, and a device configured for use with a surgical robotic arm.

The housing 613 is generally configured to be held by a human hand, and hence is of a size and shape which is compatible with the device 601 being held by a human hand. As such, the housing 613 is depicted as being ergonomically angled between the ends 615, 617, and further includes one or more of a grip portion 625 and slots, each configured for assisting a human hand with holding the housing 613.

Furthermore, while not depicted, the housing 613 may include a positioner adapter configured to be held by an arm of a device positioner and/or a robotic arm, for example a component of a surgical system, such that the arm may position the device 601 in relation to a patient being operated on, for example in relation to, and/or through, an access port and/or a surgical port. Such implementations are discussed below with respect to FIG. 18.

In some implementations, the grip portion 625 is of a shape compatible with being held by an arm of a device positioner and/or a robotic arm. In other words, the device 601 may be held in place manually by a surgeon holding the device 601, or may be configured to be held by an arm of a surgical system.

Figure 8:
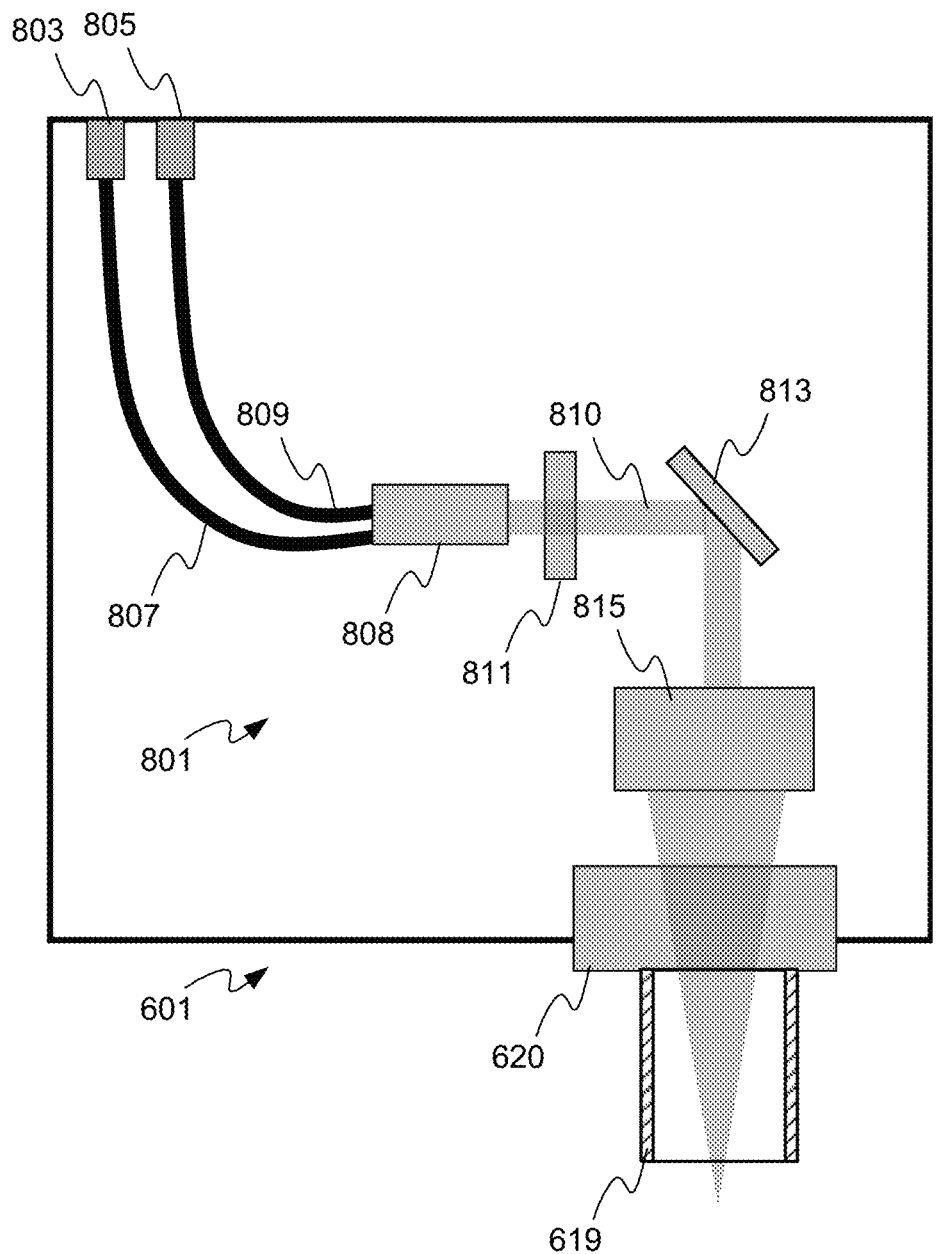
FIG. 8 depicts a block diagram of internal components of the handheld OCT device of FIG. 6, according to non-limiting implementations.

Attention is next directed to FIG. 8 which depicts a schematic block diagram of components internal to the device 601, including the OCT scanning device 801. The device 601 comprises an electrical connector 803 and an optical connector 805, removably attachable to the one or more cables 605 (e.g. of FIG. 6); the electrical connector 803 and the optical connector 805 can optionally be combined in a single connector removably attachable to the one or more cables 605. The electrical connector 803 is connected to one or more electrical cables 807, and the optical connector 805 is connected to one or more optical fibers 809 including, but not limited to, one or more PM-optical fibers. The electrical connector 803 and the one or more electrical cables 807 convey power and/or signals between the OCT interferometer 607 (and/or the computing device 609 and/or the power supply 702) and electrical components of the device 601, including, but not limited to, signals indicative of an actuation of one or more of the buttons 623. Similarly, the optical connector 805, and the one or more optical fibers 809 convey OCT light between the OCT interferometer 607 and optical components of the device 601, OCT light received from the OCT interferometer.

The one or more optical fibers 809 conveys OCT light received from the OCT interferometer 607 to collimating optics 808. Collimated OCT light is emitted from the collimating optics 808 along an optical path 810. Indeed, the optical path 810 schematically indicates a path of OCT light between the collimating optics 808 and the tip 619. In some implementations, as depicted, the OCT light is polarized; in these implementations, the OCT scanning device 801 comprises polarization optics 811, in the path 810, the polarization optics 811 configured to polarize the OCT light. For example, the polarization optics 811 can comprise a quarter wave plate.

While not depicted, in some implementations, the OCT scanning device 801 further comprises a mechanical device (e.g. a stepper motor) for moving the polarization optics 811 into and out of the path 810, for example, upon actuation of one or more of the buttons 623. Hence, in these implementations, the OCT light used for scanning is polarized or not polarized depending on a position of the polarization optics 811.

The OCT light continues along the path 810 to a scanning device 813 and a focusing device 815, which are generally configured to scan and focus the OCT light across tissue and/or a sample at the tip 619, as well as to collect light reflected from the tissue and/or the sample. The scanning device 813 comprises one or more scanning components, including, but not limited to, an acousto-optic modulator, a MEMS (microelectromechanical) mirror and a galvanometer, such scanning components configured to scan OCT light across a line and/or an area to obtain a one dimensional or two dimensional OCT image, respectively. The focusing device 815 comprises one or more lenses configured to focus the OCT light through the tip 619, as schematically indicated by the triangular shape of the path 810 between the focusing device 815 and the tip 619. Indeed, as depicted, the tip 619 is mechanically connected to the remainder of the device 601 via the adaptor 620.

In any event, OCT light reflected and/or scattered back from tissue and/or a sample at tip 619 is received back into the device 601 via the tip 619 and follows the path 810 back through the device 801 to the one or more optical fibers 809, and out the optical connector 805 to the OCT interferometer 607.

In any event, as is understood at least from FIG. 8, the OCT scanning device 801 comprises one or more of: an OCT light scanning device, an OCT light delivery apparatus, and a light polarizing apparatus.

Figure 9:
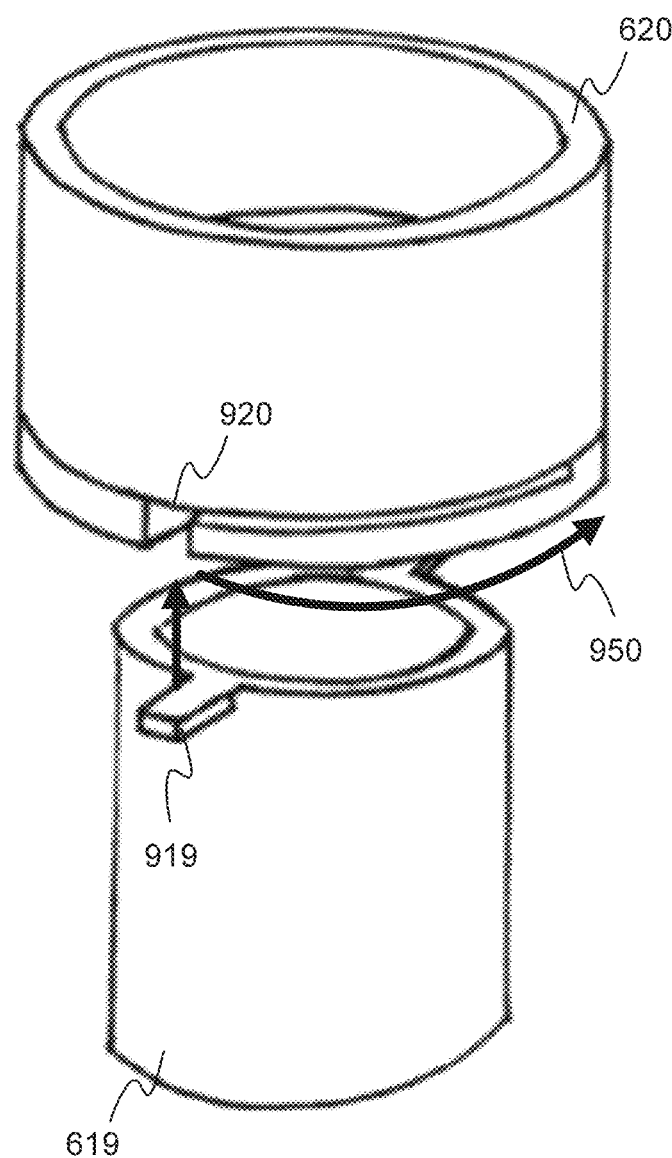
FIG. 9 depicts detail of a tip and a tissue scanning end of the handheld OCT device of FIG. 6, according to non-limiting implementations.

Attention is next directed to FIG. 9 which depicts detail of the adapter 620 and the tip 619. In particular, the tip 619 is removably attachable to the adapter 620 (e.g. the OCT scanning end 615) using one or more of: a bayonet mount; and a twist and lock attachment mechanism. For example, as depicted, the tip 619 is cylindrically shaped, at least at an attachment end (e.g. the end of the tip 619 that is to be attached to the adapter 620), and the tip 619 further comprises tabs 919 extending perpendicularly from the attachment end. The adapter 620 comprises slots 920 that are complementary to the tabs 919 such that the tabs 919 can be attached to the slots 920 by pushing the tabs 919 into the slots and then using a twist motion, as indicated by the arrows 950. Such a configuration of tabs 919 and slots 920 is referred to as a bayonet mount or, alternatively, as a twist and lock mechanism. While such a bayonet mount is useful for quickly attaching and removing the tip 619 to the device 601, especially when the surgical drape 621 extends from the tip 619, other attachment mechanisms are within the scope of present implementations, including, but not limited to, complementary threads at each of an external surface of the tip 619 and an internal surface of the adapter 620.

It is understood that the adapter 620 can be a component that is attachable to the OCT scanning end 615 (e.g. to adapt the device 601 for use with the tip 619), or the OCT scanning end 615 can be adapted to include the slots 920, for example the slots 920 can be integrated into the OCT scanning end 615. Hence, the adapter 620 is generally optional as long as the OCT scanning end 615 is adapted to include the slots 920 and/or a complementary attachment device configured to removably receive a tip.

Figure 10:
FIG. 10 depicts a tip with a surgical drape usable with the handheld OCT device of FIG. 6, according to non-limiting implementations.

Attention is next directed to FIG. 10 which depicts the tip 619 with the surgical drape 621 attached thereto, for example, bonded around an outer circumference of the tip 619 along a circumferential line 1021. The bonding can occur using any suitable technique including, but not limited to, heat bonding, glue, epoxies, and the like, assuming that the resulting combination of the tip 619 and the attached surgical drape 621 is sterilisable and biocompatible.

Indeed, in some implementations, the combination of the tip 619 and the surgical drape 621 can be provided and/or sold separately from the remainder of the device 601. Furthermore, the combination of the tip 619 and the surgical drape 621 can be sterilized, and at least the tip 619 is manufactured and/or formed from one or more materials that are both sterilisable and biocompatible. For example, materials of the tip 619 can include, but are not limited to, stainless steel, titanium, ABS-30i, and the like.

Similarly, the surgical drape 621 is generally manufactured and/or formed from one or more materials that are sterilisable including, but not limited to, various transparent and/or semi-transparent drapable plastics. Furthermore, the surgical drape 621 is generally of a shape and length that will fit over the device 601, along the one or more cables 605 to the OCT analysing system 603. Moreover, in some implementations, the surgical drape 621 can be in multiple pieces in which a first piece is configured to fit over the device 601 and a second piece is configured to fit over the cables 605; and the pieces of the surgical drape 621 can be connected using adhesives, tape, double sided tape, and the like and/or any suitable connecting material and/or sealing means.

The combination of the tip 619 and the surgical drape 621 can be sterilised and provided for a one-time use in a surgery, and/or the combination of the tip 619 and the surgical drape 621 can be used once, and then re-sterilised for another use in a surgery. Either way, combinations of tips and surgical drapes can be sold and/or provided separately from other components of the device 601.

In addition, the combination of the tip 619 and the surgical drape 621 can be provided as one of a plurality of tips, and/or different types of tips, some of which include a surgical drape, while others do not.

Figure 11:
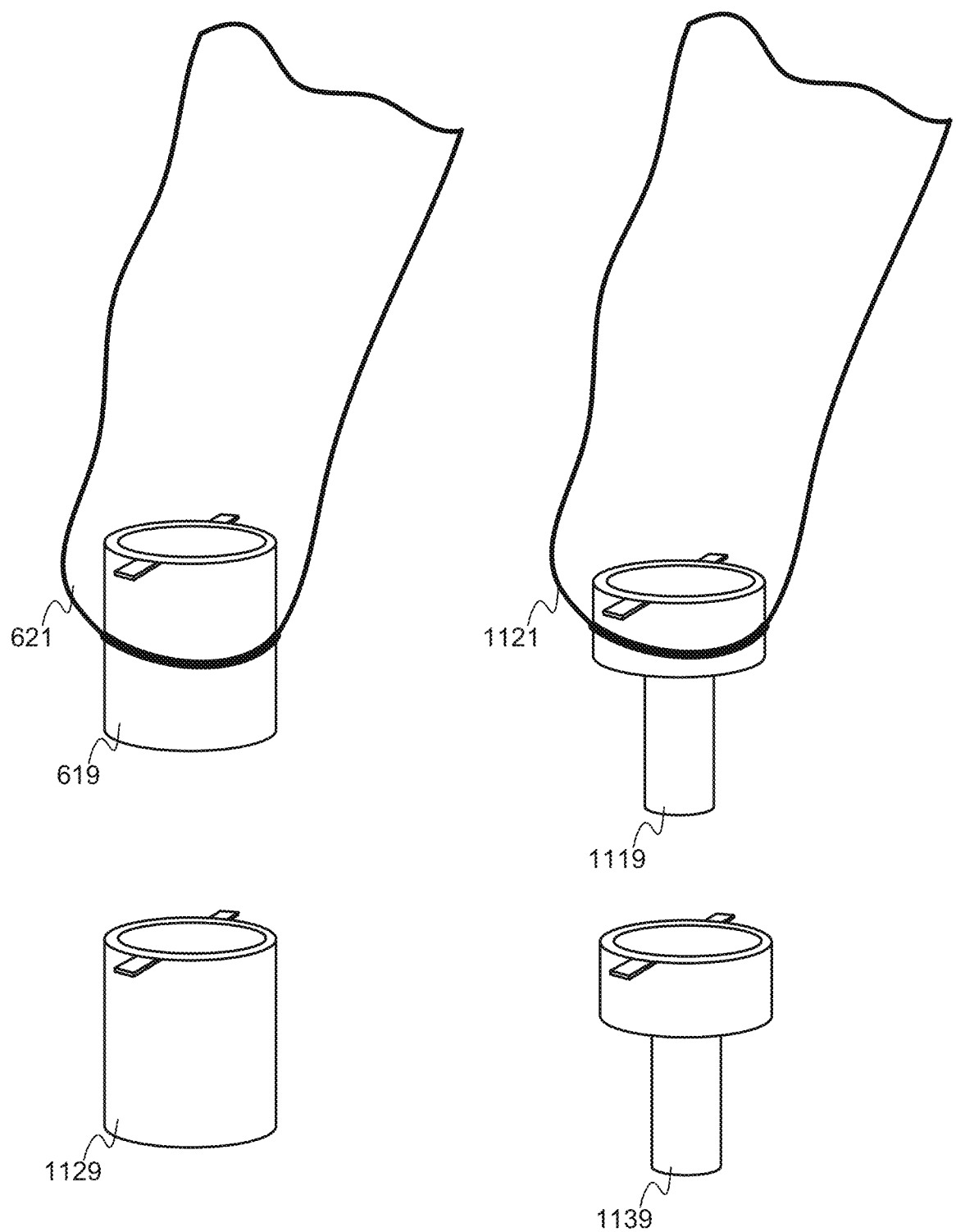
FIG. 11 depicts various tips usable with the handheld OCT device of FIG. 6, according to non-limiting implementations.

For example, attention is next directed to FIG. 11 which depicts a plurality of tips, including the combination of the tip 619 and the surgical drape 621, a combination of another tip 1119 and a respective surgical drape 1121, a tip 1129 without a surgical drape, and an alternate tip 1139 without a surgical drape. Each of the tips 619, 1129 are similar, other than the surgical drape 621 attached to the tip 619. The combination of the tip 1119 and the surgical drape 1121 is similar to the combination of the tip 619 and the surgical drape 621, other than a length and diameter of the tip 1119. For example, while an attachment end of the tip 1119 is similar to the attachment end of the tip 619, the remainder of the tip 1119 has a smaller diameter and a longer length for use, for example, for use with a surgical port and/or to access a deeper part of a surgical field. In other words, the tip 619 may be used with open case surgery, while the tip 1119 may be swapped onto the adapter 620 to adapt the device 601 for use with a surgical port. Similarly, the tips 1119, 1139 can be used on skin in a diagnostic environment, with or without sterilization, for example on the surface of a patient's skin (e.g. not during surgery).

Hence a wide variety of shapes and sized of tips for the device 601 are within the scope of present implementations. For example, for use with open case surgery, such tips can be between about 0.5 inches and about 3 inches in length, and such tips can have an outer diameter that is between about 1 mm and about 15 mm (e.g. other than at an attachment end). For use with surgical access ports, such tips can be between about 3 inches and about 15 inches in length (e.g. longer than a surgical access port with which such tips are to be used), and such tips can have an outer diameter that is between about 1 mm and about 10 mm (e.g. less than an inner diameter of a surgical access port with which such tips are to be used).

However, the attachment ends of the tips 619, 1119, 1129, 1139 are all similar (e.g. similar tabs, similar diameters) such that the tips 619, 1119, 1129, 1139 are all usable with the adapter 620. Put another way, the OCT scanning end 615 is configured (e.g. by way of the adapter 620 and/or slots 920) for removeable attachment to one of a plurality of tips. In some implementations, each of the plurality of tips comprises a respective surgical drape attached around a respective outer circumference, the respective surgical drape configured to extend from a respective tip, over the housing 613 and past the proximal end 617 of the housing 613, for example to the OCT analysing system 603.

As depicted, each of the tips 619, 1119, 1129, 1139 are cylindrical in shape and can be hollow. However, the tips 619, 1119, 1129, 1139 can include windows, lenses, lens systems, and/or other types of optical components, and the like, internally.

Figure 12:
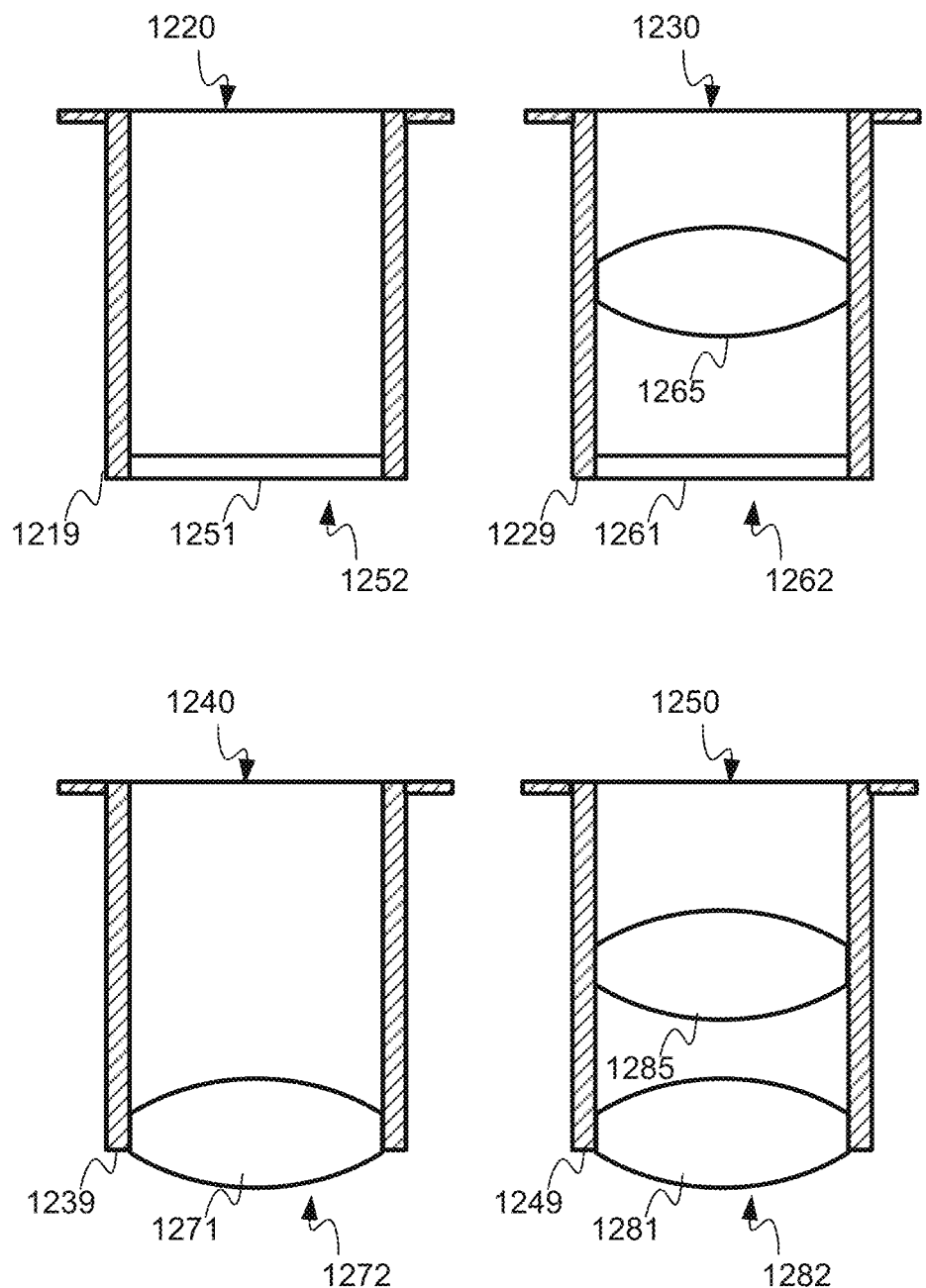
FIG. 12 depicts cross-sections of various tips usable with the handheld OCT device of FIG. 6, according to non-limiting implementations.

For example, attention is next directed to FIG. 12 which depicts cross-sections of other tips 1219 (having an attachment end 1220), 1229 (having an attachment end 1230), 1239 (having an attachment end 1240), 1249 (having an attachment end 1250), through a lateral cross-section that includes respective tabs at a respective attachment end. The tips 1219, 1229, 1239, 1249 are generally similar to the tips 619, 1129, however the tips 1219, 1229, 1239, 1249 each include optical components, for example at a respective tissue end (e.g. opposite a respective attachment end, the tissue end comprising the end of a tip that interacts with tissue and/or a sample) and/or internally.

For example, the tip 1219 includes a window 1251 transparent to OCT light at a tissue end 1252. The tip 1229 includes a window 1261 transparent to OCT light at a tissue end 1262, and a lens 1265 internal to the tip 1229, the lens 1265 configured to focus OCT light, for example in conjunction with the focusing element 815. The tip 1239 includes a lens 1271 transparent to OCT light at a tissue end 1272, the lens 1271 configured to focus OCT light, for example in conjunction with the focusing element 815. The tip 1249 includes a lens 1281 transparent to OCT light at a tissue end 1282, and a lens 1285 internal to the tip 1249; together the lenses 1281, 1285 form a lens system, the lens system configured to focus OCT light, for example in conjunction with the focusing element 815. It is appreciated that the windows 1251, 1261, and the lenses 1271, 1281 are each formed from materials that are both sterilisable and biocompatible as the windows 1251, 1261, and the lenses 1271, 1281 may generally come into contact with tissue. The optical components internal to the tips are also sterilisable and, in some implementations, also biocompatible; however, as the internal optical components may not come into contact with tissue, their biocompatibility (and their sterilisablitity) is less important then with the windows 1251, 1261, and the lenses 1271, 1281.

Indeed, the tips 1219, 1229, 1239, 1249 depicted in FIG. 12 illustrate that a wide variety of tips, having various optical components, are within the scope of present implementations. Furthermore, other tips, having other optical components, will occur to persons of skill in the art and are within the scope of present implementations. For example, in some implementations, a tip usable with the device 601 is not hollow but filled with an optically transparent material.

Furthermore, the windows 1251, 1261, and the lenses 1271, 1281, and the like, provided at their respective tissue ends can be used to provide stability to the device 601 when used, for example against tissue. For example, when the device 601 is held by a surgeon and pressed against tissue, the windows 1251, 1261, and the lenses 1271, 1281, and the like at the end of a tip can planarize the tissue (at least in the case of the windows 1251, 1261) and act as a stabilization area against which the surgeon can hold the device 601 steady, relative to the tissue. Indeed, use of a window, a lens, and the like, at a tissue end of any of the tips described herein can provide stability against both macro-movement, and micromovement, including, but not limited to, lateral movement, of the device 601, which can important when using the device in one or more of a polarization OCT scanning mode, and a Doppler OCT scanning mode.

Figure 13:
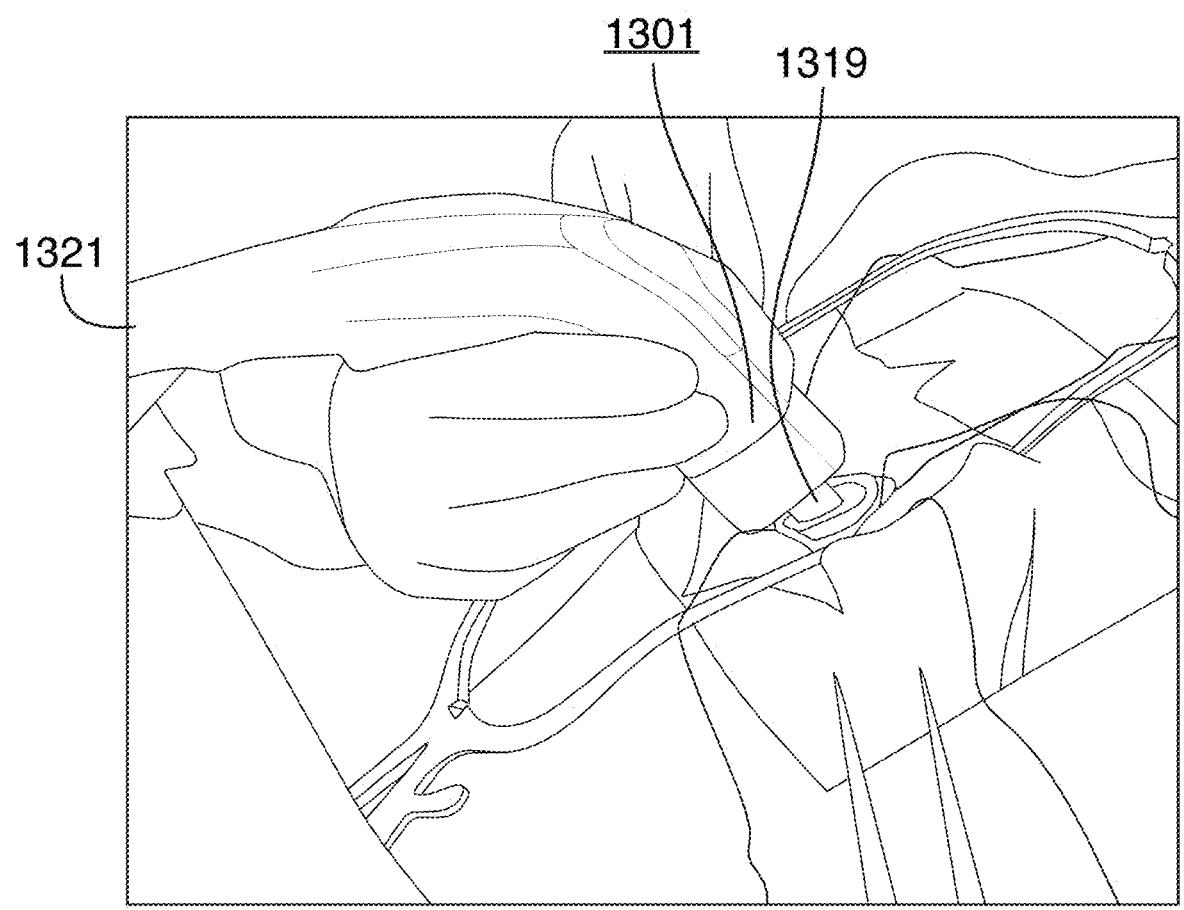
FIG. 13 depicts a prototype of a handheld OCT device in use, according to non-limiting implementations.

For example, attention is next directed to FIG. 13 which depicts a prototype device 1301 in use performing OCT scanning of a pig's brain. The prototype device 1301 is similar to device 601, though with a housing having a shape different from the housing 613; however, the device 1301 includes a tip 1319, similar to the tip 619, and a surgical drape 1321, similar to the surgical drape 621, extending from the tip 1319, over the device 1301, and cables extending therefrom, for example to an OCT analyzing system. The device 1301 is not sterilized, other than the tip 1319, and the surgical drape 1321, and furthermore, the device 1301 successfully performs both polarization OCT scanning and Doppler OCT scanning, as described above, in an open case surgery environment.

Figure 14:
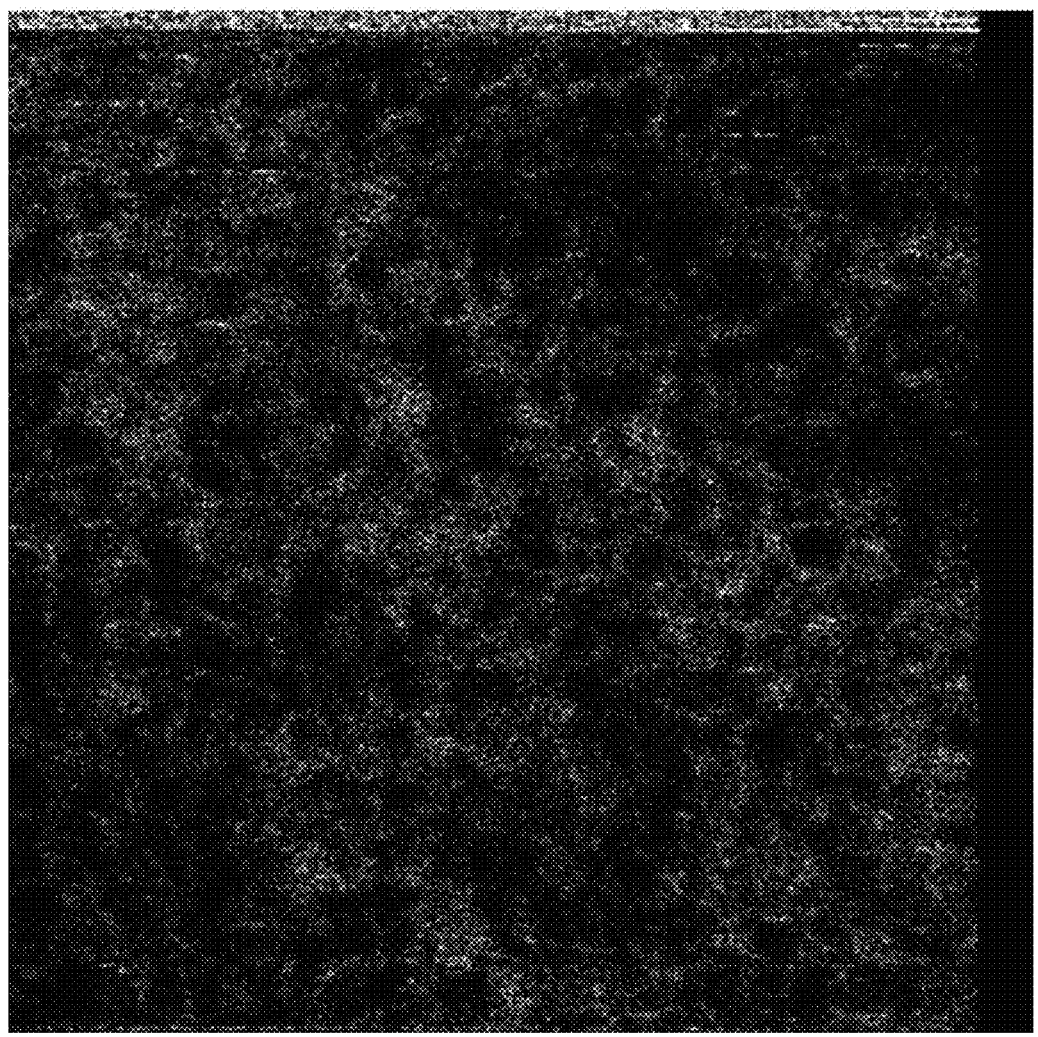
FIG. 14 depicts an en-face Doppler OCT image acquired using a prototype of a handheld OCT device, according to non-limiting implementations.
Figure 15:
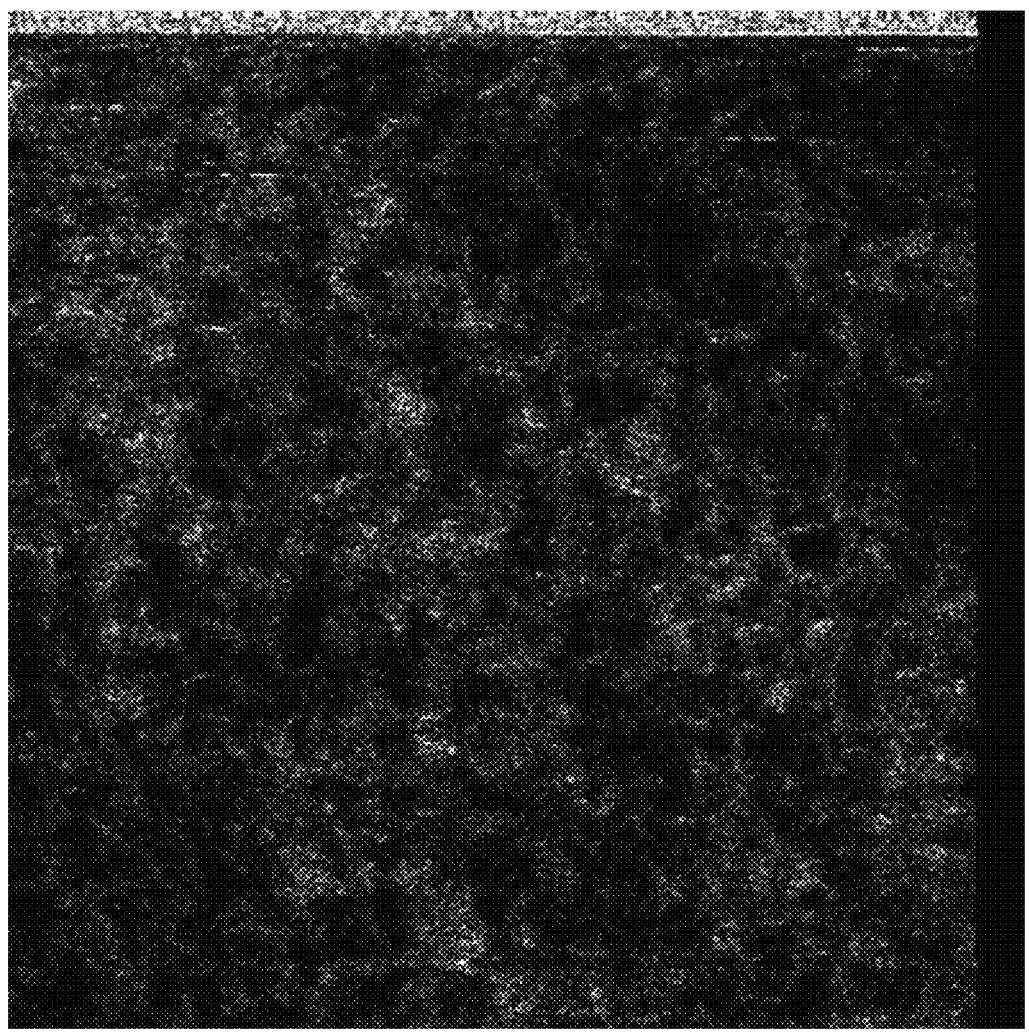
FIG. 15 depicts a P-State Polarization en-face Doppler OCT image acquired using a prototype of a handheld OCT device, according to non-limiting implementations.
Figure 16:
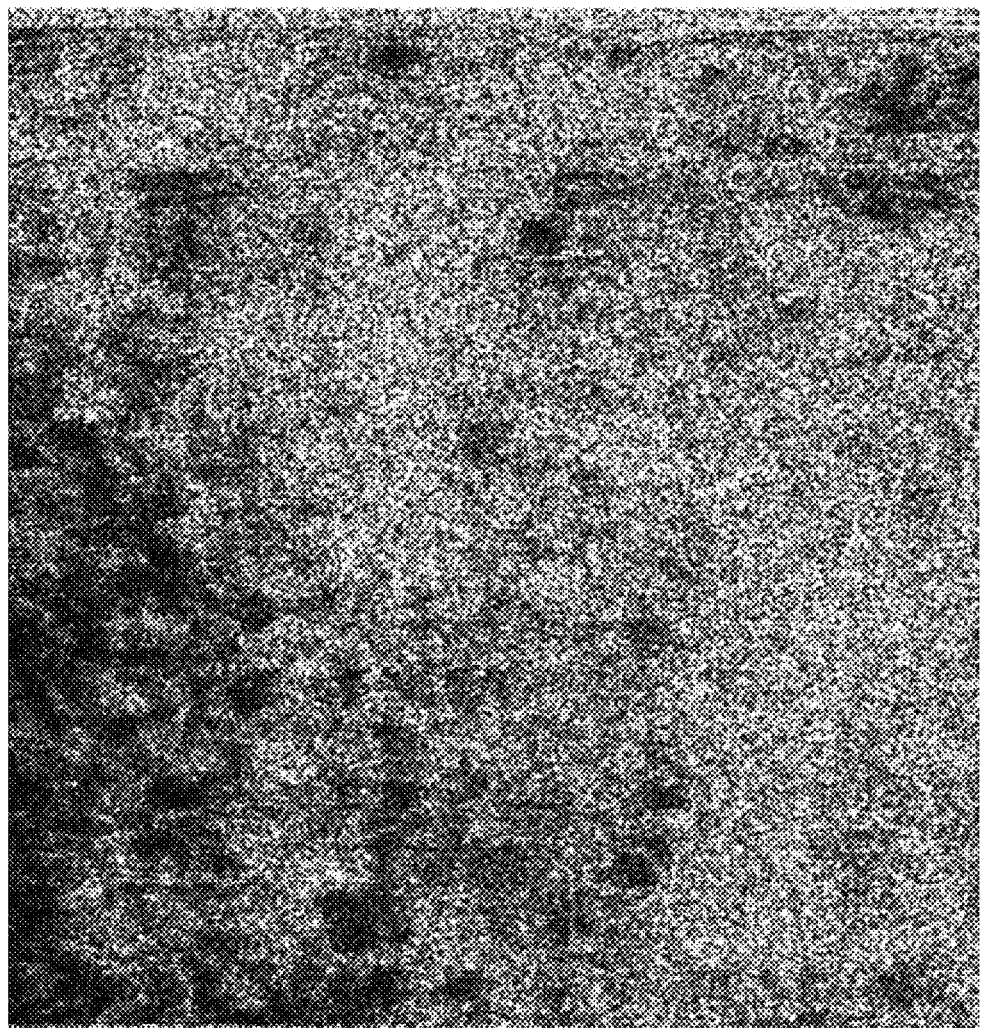
FIG. 16 depicts an S-State Polarization en-face Doppler OCT image acquired using a prototype of a handheld OCT device, according to non-limiting implementations.

Indeed, attention is next directed to FIG. 14, FIG. 15, and FIG. 16 which respectively depict: a Doppler OCT image 1401 obtained using a device similar to the device 601 operated in a Doppler mode; a P-Polarization State Doppler image 1501 obtained using the device operated in a polarization Doppler mode; and an S-Polarization State Doppler image 1601 obtained using the device operated in the polarization Doppler mode. Indeed, for each of the images 1401, 1501, 1601, skin of a human being was scanned using the device while being hand-operated. In any event, as each of the images 1401, 1501, 1601 is not blurry, the images 1401, 1501, 1601 illustrate that devices used herein can provide sufficient stability to perform Doppler OCT scanning and polarization OCT scanning using a handheld OCT device. Furthermore, different types of information are available in each of the images 1401, 1501, 1601, for example, blood flow information, tissue organization and the like.

Figure 17:
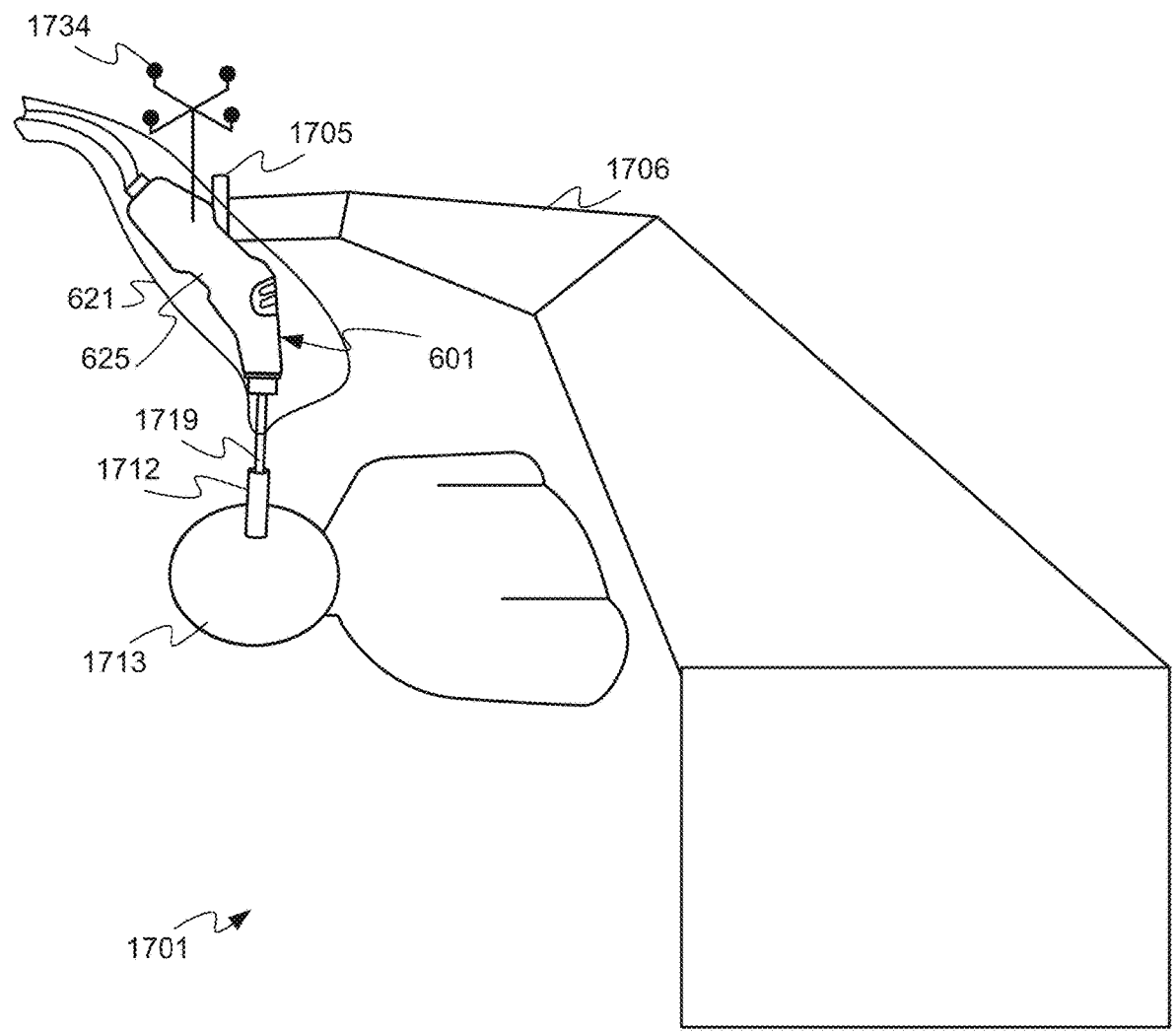
FIG. 17 depicts the handheld OCT device of FIG. 6 in use with a device positioning system in a surgical environment, according to non-limiting implementations.

Attention is next directed to FIG. 17 which schematically depicts the device 601 in use with a device positioning system 1701. In particular, a device positioning system 1701 includes a coupler 1705 configured to couple to the device 601 to an arm 1706 of the device positioning system 1701. Hence, while not depicted, device 601 may comprise one or more mechanical connectors and/or positioner adapters configured to attach the device 601 to a mechanical arm of a surgical system, for example that includes device positioning system 1701. Furthermore, in some implementations, the coupler 1705 is configured to hold the device 601 by the grip portion 625.

As depicted, the surgical drape 621 covers the device 601, and the coupler 1705 can couple to the device 601, for example through an aperture in the surgical drape 621. However, the surgical drape 621 may be present or absent, as desired, for example according to the sterilization needs of the use of the device 601 with the device positioning system 1701. Either way, at least a tip 1719 of the device 601 is sterilized, the tip 1719 being similar to the tip 619 but configured for use with a surgical access port 1712.

In particular, the device 601 is positioned with respect to a surgical access port 1712 that has been placed in a patient 1713 (as with access port 12 in FIG. 5), so that tissue therein is accessible. In particular, device positioning system 1701 may position the tip 1719 of the device 601 into the surgical access port 1712. Hence, the robotic arm 1706 may be controlled to position the tip 1719 into the surgical access port 1712 so that device 601 may perform one or more OCT scans on tissue of the patient 1713; for example, while not depicted, the computing device 609 may be in communication with the device positioning system 1701 and control the device positioning system 1701 to position the tip 1719 into the surgical access port 1712.

As depicted, the device 601 has been adapted to include a tracking device 1734, which can include, but is not limited, to the tracking device 704.

The tracking device 1734 is located at a proximal end of the device 601. Furthermore, the tracking device 1734 extends through the surgical drape 621 (e.g. through an aperture therein).

The tracking device 1734 is generally configured to be tracked by a surgical navigation system, which can include, but is not limited to, components of the device positioning system 1701. The tracking device 1734 is generally to extend away from the device 601 so that a camera, and the like, of the surgical navigation system may track a position of the tracking device 1734 and hence a position of the device 601. As depicted, the tracking device 1734 comprises four reflective spheres arranged in a configuration where each sphere is located at about a corner of a square. However, other numbers of spheres and other configurations are within the scope of present implementations. For example, in some implementations, three or more of such spheres may be arranged and configured and/or selected to provide a given tracking accuracy, including, but not limited to, a tracking accuracy that is less than about half a diameter of a sensing array surface. However, the tracking device 1734 may include tracking devices other than reflective spheres. For example, in some implementations, the tracking device 1734 may include a flexible sheath configured to measure tip position deflection, for example deflection of a tip of the flexible sheath. Furthermore, the device 601 may be adapted to include one or more tracking devices.

Figure 18:
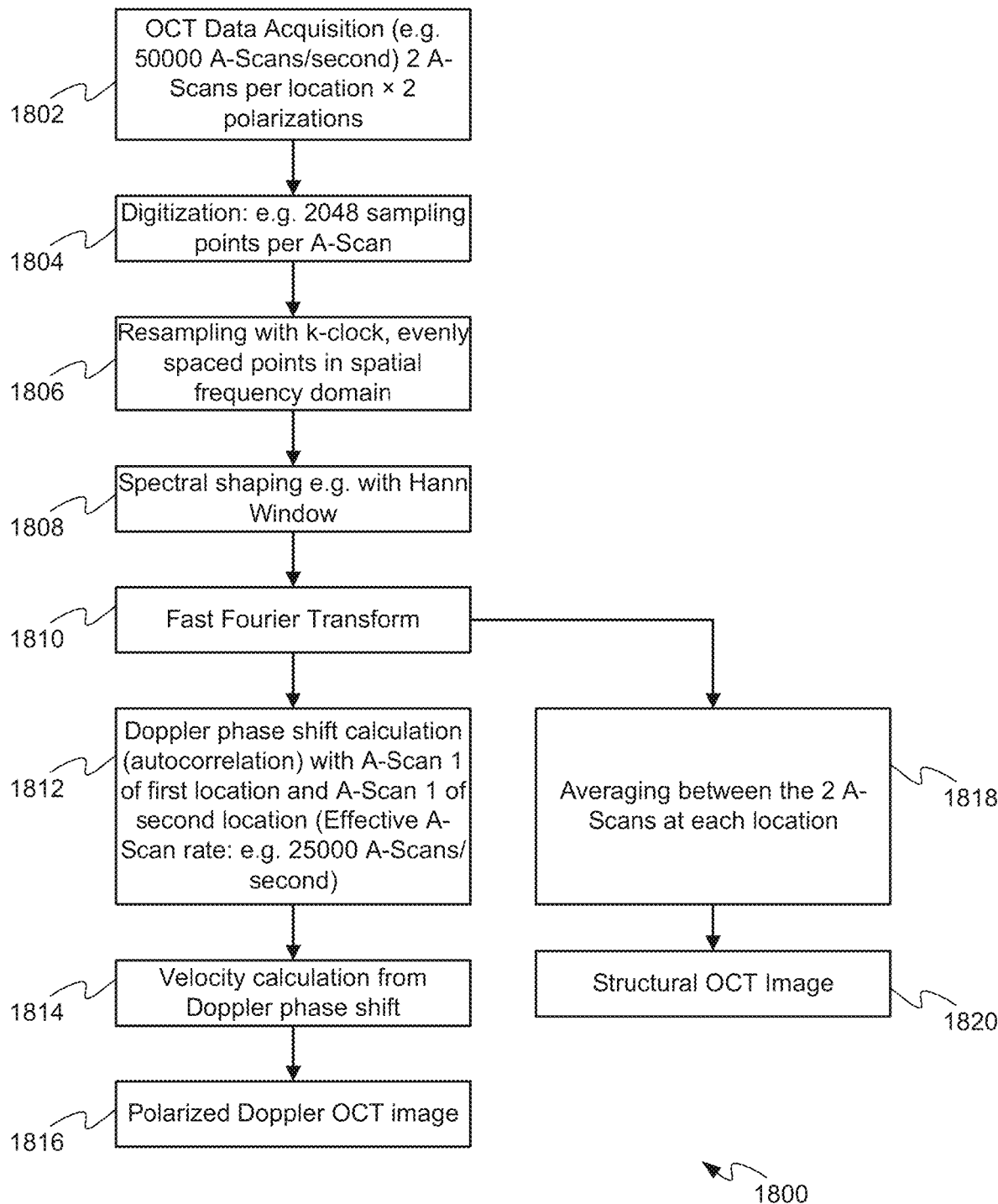
FIG. 18 depicts a block diagram of a method for acquiring OCT images using the system of FIG. 6, according to non-limiting implementations.

Attention is now directed to FIG. 18, which depicts a flowchart of a method 1800 for generating OCT images using the system 600, according to non-limiting implementations. In order to assist in the explanation of the method 1800, it will be assumed that the method 1800 is performed using the computing device 609. Indeed, the method 1800 is one way in which the computing device 609 can be configured. Furthermore, the following discussion of the method 1800 will lead to a further understanding of the system 600 and its various components. However, it is to be understood that the system 600 and/or the method 1800 can be varied, and need not work exactly as discussed herein in conjunction with each other, and that such variations are within the scope of present implementations. In other words, the method 1800 is one of various techniques used to operate the system 600 to generate OCT images, and other techniques are within the scope of the present specification.

Regardless, it is to be emphasized, that the method 1800 need not be performed in the exact sequence as shown, unless otherwise indicated; and likewise various blocks may be performed in parallel rather than in sequence; hence the elements of the method 1800 are referred to herein as "blocks" rather than "steps". It is also to be understood, however, that the method 1800 can be implemented on variations of the device 601 as well. Furthermore, while the computing device 609 is described as implementing and/or performing each block of the method 1800, it is appreciated that one or more blocks of the method 1800 occurs in conjunction with the device 601 and/or the OCT interferometer 607.

At a block 1802, the computing device 609 initiates OCT data acquisition, for example for two polarization states (e.g. the s-state and the p-state), by causing the device 601 and the OCT interferometer 607 to perform OCT scanning using polarization optics 811 in the path 810. The block 1802 can occur upon receipt of a signal from the device 601 that indicates that one or more of the buttons 623 has been actuated. Furthermore, in some implementations, the OCT signal acquisition comprises 50000 A-scans per second per location (e.g. for each location of tissue scanned using the device 601), and for each of the polarization states. However, other numbers of A-scans per second are within the scope of the present specification. Furthermore, the block 1802 results in two polarization OCT data sets (e.g. an s-state OCT data set and a p-state OCT data set).

At a block 1804, the computing device 609 digitizes the OCT data acquired for each of the polarization data sets using, for example, 2048 sampling points per A-Scan, however other numbers of sampling points are within the scope of the present specification.

At a block 1806, the computing device 609 resamples the digitized OCT data of each of the polarization data sets, generated at the block 1804, for example, using k-clock sampling to resample evenly spaced points in the digitized OCT data in the spatial frequency domain. In general, k-clock sampling comprises a sampling of points and/or locations in a signal, such that these points and/or locations are equally spaced in the spatial frequency domain (e.g. as opposed to a wavelength domain of the signal).

At a block 1808, the computing device 609 optionally performs spectral shaping of each of the resampled digitized OCT data generated at the block 1806, for each polarization data set, using, for example, a Hann Window, though other techniques for performing spectral shaping are within the scope of the present specification.

At a block 1810, the computing device 609 performs a fast Fourier transform on each of the spectrally shaped resampled digitized OCT data, for each polarization data set.

The computing device 609 may implement blocks 1812-1816 to produce Polarized Doppler OCT Images for each polarization data set using the transformed spectrally shaped resampled digitized OCT data produced at the block 1810 (e.g. as with images 1501, 1601); and/or the computing device 609 may implement blocks 1818-1820 to produce Polarized OCT Images (e.g. without Doppler) for each polarization data set using the transformed spectrally shaped resampled digitized OCT data produced at the block 1810.

For example, at block 1812, the computing device 609 performs a Doppler phase shift calculation (e.g. using autocorrelation) using A-scans of two locations in the transformed spectrally shaped resampled digitized OCT data produced at the block 1810. For example, phases of adjacent locations in the spectrally shaped resampled digitized OCT data are compared by autocorrelation to determine frequency phase shifts therebetween. With typical A-scan averaging of, for example two locations the resulting Doppler OCT data set has an effective scan rate of about half the scan rate used to acquire the OCT at the block 1802 (e.g. if a scan rate of 50000 A-scans per second was used at the block 1802, the effective scan rate of Doppler OCT data produced at the block 1812 is 25000 A-scans per second). Furthermore, the Doppler phase shift calculations occur for each of the two polarization data sets.

At a block 1814, the computing device determines velocity differences between each of the adjacent locations from the Doppler phase shifts determined at the block 1812 for each of the polarization data sets, and produces Polarized Doppler OCT images at the block 1816 for each of the polarization data sets (e.g. similar to the images 1501, 1601). The images can be stored in a memory of the computing device 609, and/or output to the display device 611 for viewing by a surgeon, and the like, handling and/or using the device 601 (whether by hand, or via a device positioning system and the like).

Alternatively, and/or in addition to generating Polarized Doppler OCT images, the computing device 609, can generate polarized structural OCT images for each of the polarization data sets without Doppler analysis. In these implementations, at a block 1818, the computing device 609 averages the transformed spectrally shaped resampled digitized OCT data produced at the block 1810 for each A-scan at each location scanned. At a block 1820, the computing device 609 generates structural OCT images for each of the polarization data sets from the averages produced at the block 1818.

While not depicted, in some implementations, the method 1800 can optionally include the computing device 609 generating non-polarized Doppler OCT images (e.g. as in the image 1401) and/or non-polarized non-Doppler OCT images (e.g. "traditional" OCT images).

While features of OCT systems and probes are described with reference to specific implementations, features described with reference to one implementation of an OCT system and/or probe and/or device may be used with other implementations of OCT systems and/or probes and/or devices. For example, any of the OCT systems and/or probes and/or devices described herein may be adapted to include anti-reflective coatings, immersion materials, index matching materials, further tracking devices, and the like. Furthermore, while present implementations have been described with reference to port-based surgery and open case surgery, present implementations may be used other types of surgery that is not port-based including, but not limited to open cranial surgery, and the like.

Described herein is a handheld OCT device with various functions and/or modalities, including polarized OCT scanning and/or Doppler OCT scanning, the handheld OCT device provided with stability using a removeable tip. The tip can include a surgical drape extending therefrom that covers the handheld OCT device, and which can hence quickly adapt the handheld OCT device for sterilized use in a surgical environment.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An OCT (Optical Coherence Tomography) handheld device comprising:
    a housing comprising: a grip portion; a button to initiate an OCT scan when actuated; an OCT scanning end; and a proximal end;
    an OCT scanning device, in the housing, to: perform the OCT scan from the OCT scanning end when the button is actuated; and receive and convey OCT light between the proximal end and an OCT analyzing system;
    at least one cylindrical hollow tip, extending from the OCT scanning end, to collect the OCT light, and comprising: a tissue end to interact with tissue during a surgical procedure; a lens internal to the at least one cylindrical hollow tip, and to focus the OCT light; and, at the tissue end, an OCT light-transparent window to planarize the tissue and to mechanically stabilize the housing in relation to the tissue;
    at least one adapter to removably couple the at least one cylindrical hollow tip with the OCT scanning device;
    at least one surgical drape comprising: a distal portion to couple with an outer circumference portion of the at least one cylindrical hollow tip; and a proximal portion, the at least one surgical drape extending from the outer circumference portion, over the housing and beyond the proximal end of the housing to the proximal portion; and
    at least one coupler to couple the OCT scanning device with a robotic arm of a device positioning system through an aperture of the at least one surgical drape between the distal portion and the proximal portion,
    wherein the at least one cylindrical hollow tip is removably coupled with the at least one adapter by a bayonet mount.

2. The OCT handheld device of claim 1, wherein the at least one surgical drape is further to extend over at least one cable extending from the proximal end to the OCT analyzing system.

3. The OCT handheld device of claim 1, wherein the at least one cylindrical hollow tip comprises a length in a range of approximately 0.5 inch to approximately 3 inches.

4. The OCT handheld device of claim 1, wherein the at least one cylindrical hollow tip comprises an outer diameter in a range of approximately 1 mm to approximately 15 mm.

5. The OCT handheld device of claim 1, wherein the at least one cylindrical hollow tip comprises a length in a range of approximately 3 inches to approximately 15 inches in length.

6. The OCT handheld device of claim 1, wherein the at least one cylindrical hollow tip comprises an outer diameter in a range of approximately 1 mm to approximately 10 mm.

7. The OCT handheld device of claim 1, wherein the OCT scanning device is further configured to perform polarized OCT scanning.

8. The OCT handheld device of claim 1, wherein the OCT scanning device comprises at least one of: an OCT light scanning device, an OCT light delivery apparatus, and a light polarizing apparatus.

9. The OCT handheld device of claim 1, wherein the OCT scanning device comprises polarization optics configured to polarize the OCT light.

10. The OCT handheld device of claim 9, wherein the polarization optics comprises a quarter waveplate.

11. The OCT handheld device of claim 9, further comprising at least one polarization-maintaining optical fiber to transmit and receive the OCT light in relation to the OCT analyzing system.

12. The OCT handheld device of claim 1, further comprising a tracking device.

13. The OCT handheld device of claim 1, wherein at least one cylindrical hollow tip comprises a plurality of cylindrical hollow tips.

14. The OCT handheld device of claim 13, wherein each cylindrical hollow tip of the plurality of cylindrical hollow tips comprises a distinct dimension in relation to another cylindrical hollow tip of the plurality of cylindrical hollow tips.

15. The OCT handheld device of claim 13, wherein each cylindrical hollow tip of the plurality of cylindrical hollow tips comprises a distinct shape in relation to another cylindrical hollow tip of the plurality of cylindrical hollow tips.

16. The OCT handheld device of claim 1, wherein the window comprises a material that is at least one of sterilizable and biocompatible.

17. The OCT handheld device of claim 1,
wherein the at least one cylindrical hollow tip comprises at least one material of: stainless steel, titanium, and ABS-30i, and
wherein the at least one cylindrical hollow tip comprises a material that is at least one of sterilizable, biocompatible, and single-use.

18. The OCT handheld device of claim 1,
wherein each at least one cylindrical hollow tip further comprises a plurality of tabs radially extending perpendicularly from an attachment end,
wherein each at least one adapter comprises a plurality of slots to complementarily couple with the plurality of tabs, and
wherein the plurality of the tabs are to couple with the plurality of slots by: disposing the plurality of tabs in the plurality of slots; and twisting each at least one cylindrical hollow tip in relation to each at least one adapter.

19. The OCT handheld device of claim 1, wherein the at least one surgical drape comprises a plastic material, and wherein the at least one surgical drape is one of sterilizable and single-use.

20. The OCT handheld device of claim 1, further comprising:
at least one polarization-maintaining optical fiber to transmit and receive the OCT light in relation to the OCT analyzing system; and
a tracking device,
wherein the at least one surgical drape is further to extend over at least one cable extending from the proximal end to the OCT analyzing system,
wherein the OCT scanning device is further to perform polarized OCT scanning,
wherein the OCT scanning device comprises at least one of an OCT light scanning device, an OCT light delivery apparatus, and a light polarizing apparatus,
wherein the OCT scanning device comprises polarization optics to polarize the OCT light,
wherein the polarization optics comprises a quarter waveplate,
wherein the at least one cylindrical hollow tip comprises a plurality of cylindrical hollow tips,
wherein each cylindrical hollow tip of the plurality of cylindrical hollow tips comprises a distinct dimension in relation to another cylindrical hollow tip of the plurality of cylindrical hollow tips,
wherein each cylindrical hollow tip of the plurality of cylindrical hollow tips comprises a distinct shape in relation to another cylindrical hollow tip of the plurality of cylindrical hollow tips,
wherein the window comprises a material that is at least one of sterilizable and biocompatible,
wherein the at least one cylindrical hollow tip comprises a material that is at least one of sterilizable, biocompatible, and single-use,
wherein each at least one cylindrical hollow tip further comprises a plurality of tabs radially extending perpendicularly from an attachment end,
wherein each at least one adapter comprises a plurality of slots to complementarily couple with the plurality of tabs,
wherein the plurality of the tabs are to couple with the plurality of slots by: disposing the plurality of tabs in the plurality of slots; and twisting each at least one cylindrical hollow tip in relation to each at least one adapter, and
wherein the surgical procedure comprises a neurosurgical procedure.

* * * * *